(12) United States Patent
Chen et al.

(10) Patent No.: US 9,315,836 B2
(45) Date of Patent: *Apr. 19, 2016

(54) FATTY ACID DESATURASE USED IN THE BIOSYNTHESIS OF LONG CHAIN OMEGA-3 POLYUNSATURATED FATTY ACIDS

(71) Applicant: University of Jiangnan, Wuxi (CN)

(72) Inventors: Haiqin Chen, Wuxi (CN); Zhennan Gu, Wuxi (CN); Hao Zhang, Wuxi (CN); Wei Chen, Wuxi (CN); Yuanda Song, Wuxi (CN); Fengwei Tian, Wuxi (CN); Jianxin Zhao, Wuxi (CN); Yongquan Chen, Wuxi (CN)

(73) Assignee: University of Jiangnan, Wuxi (CN)

( * ) Notice: Subject to any disclaimer, the term of this patent is extended or adjusted under 35 U.S.C. 154(b) by 46 days.

This patent is subject to a terminal disclaimer.

(21) Appl. No.: 14/324,099

(22) Filed: Jul. 4, 2014

(65) Prior Publication Data
US 2014/0363860 A1 Dec. 11, 2014

Related U.S. Application Data

(62) Division of application No. 13/646,667, filed on Oct. 6, 2012, now Pat. No. 8,962,276.

(51) Int. Cl.
*C12N 9/00* (2006.01)
*C12N 15/52* (2006.01)
*C12P 7/64* (2006.01)
*C12N 9/02* (2006.01)

(52) U.S. Cl.
CPC .............. *C12P 7/6427* (2013.01); *C12N 9/0071* (2013.01); *C12N 9/0083* (2013.01); *C12Y 114/19001* (2013.01); *Y02P 20/52* (2015.11)

(58) Field of Classification Search
CPC ........ C12N 9/00; C12N 15/00; C12N 9/0083; C12N 15/52; C12P 7/6409
See application file for complete search history.

(56) References Cited

PUBLICATIONS

Sakuradani et al. 2005; A novel fungal omega 3—desaturase with wide substrate specificity from arachidonic acid-producing Mortierella alpine 1S-4. Applied Microbiology and Biotechnology. 66: 648-654.*

* cited by examiner

*Primary Examiner* — Karen Cochrane Carlson
(74) *Attorney, Agent, or Firm* — CBM Patent Consulting, LLC

(57) ABSTRACT

The present invention provides novel fatty acid desaturases genes used for synthesis of polyunsaturated fatty acids, especially ω3 desaturases (FADS15). The present invention also provides nucleic acid sequence coding the above-described desaturases, expression vector of the above-described desaturases and recombinant microorganism expressing above-described desaturases.

4 Claims, 24 Drawing Sheets

Fig. 2D

Fig. 3A

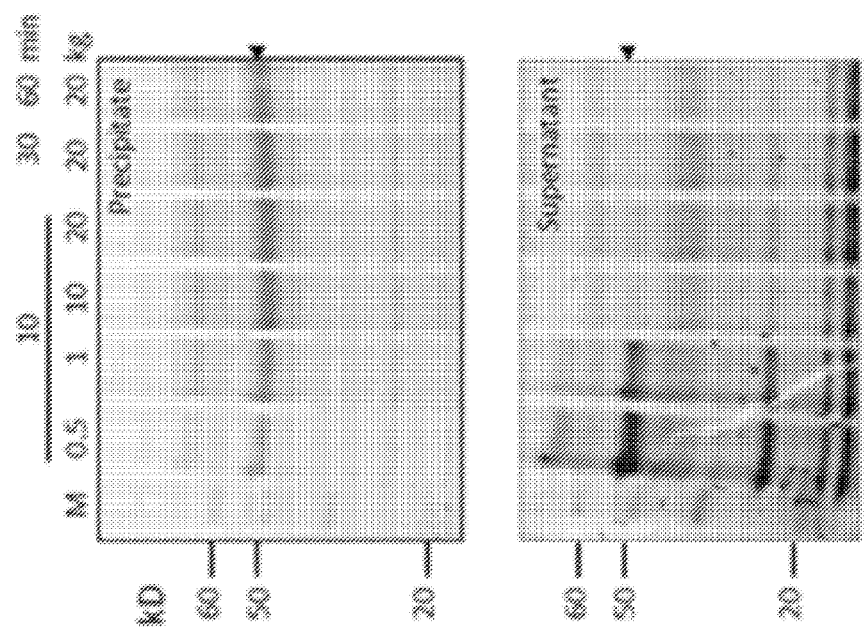

Figure 1:
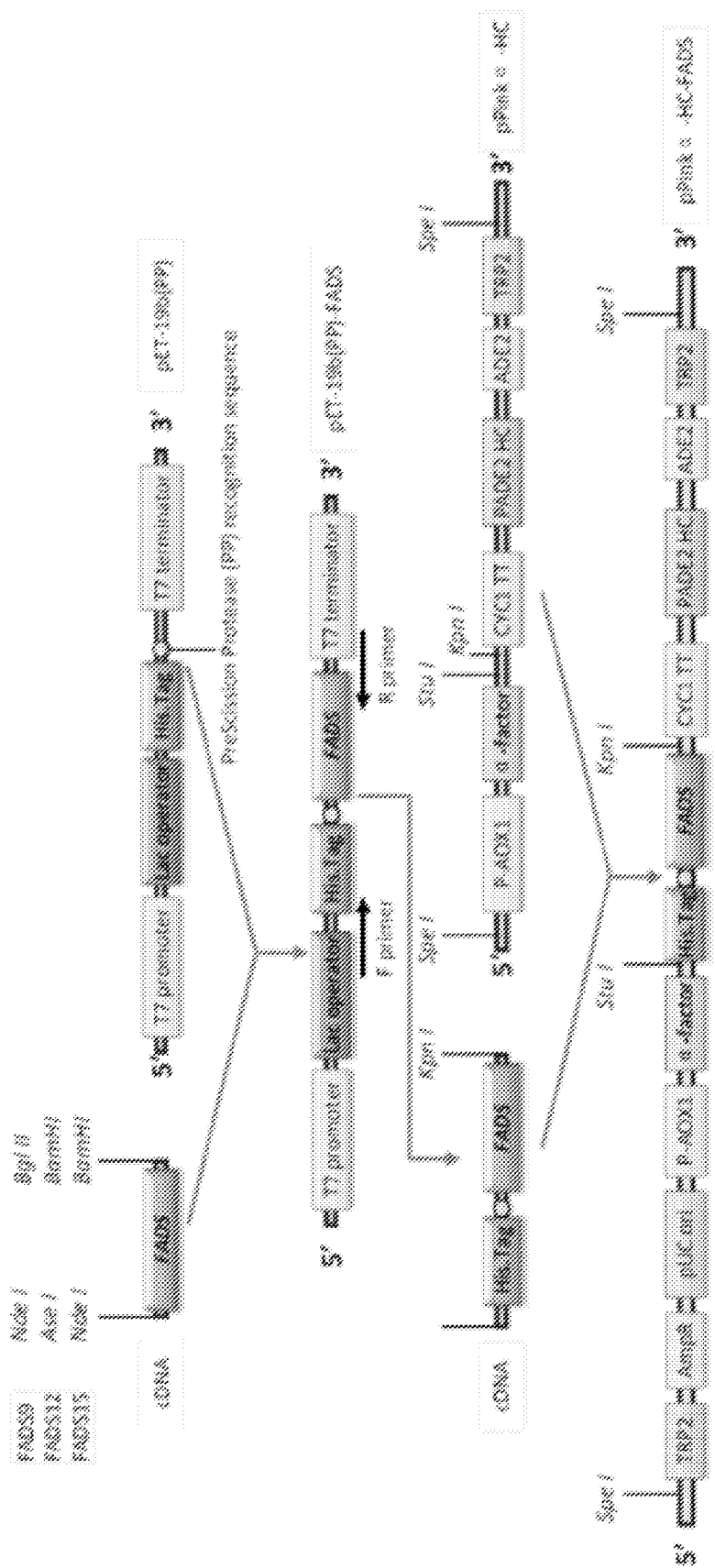
Figure 2A:
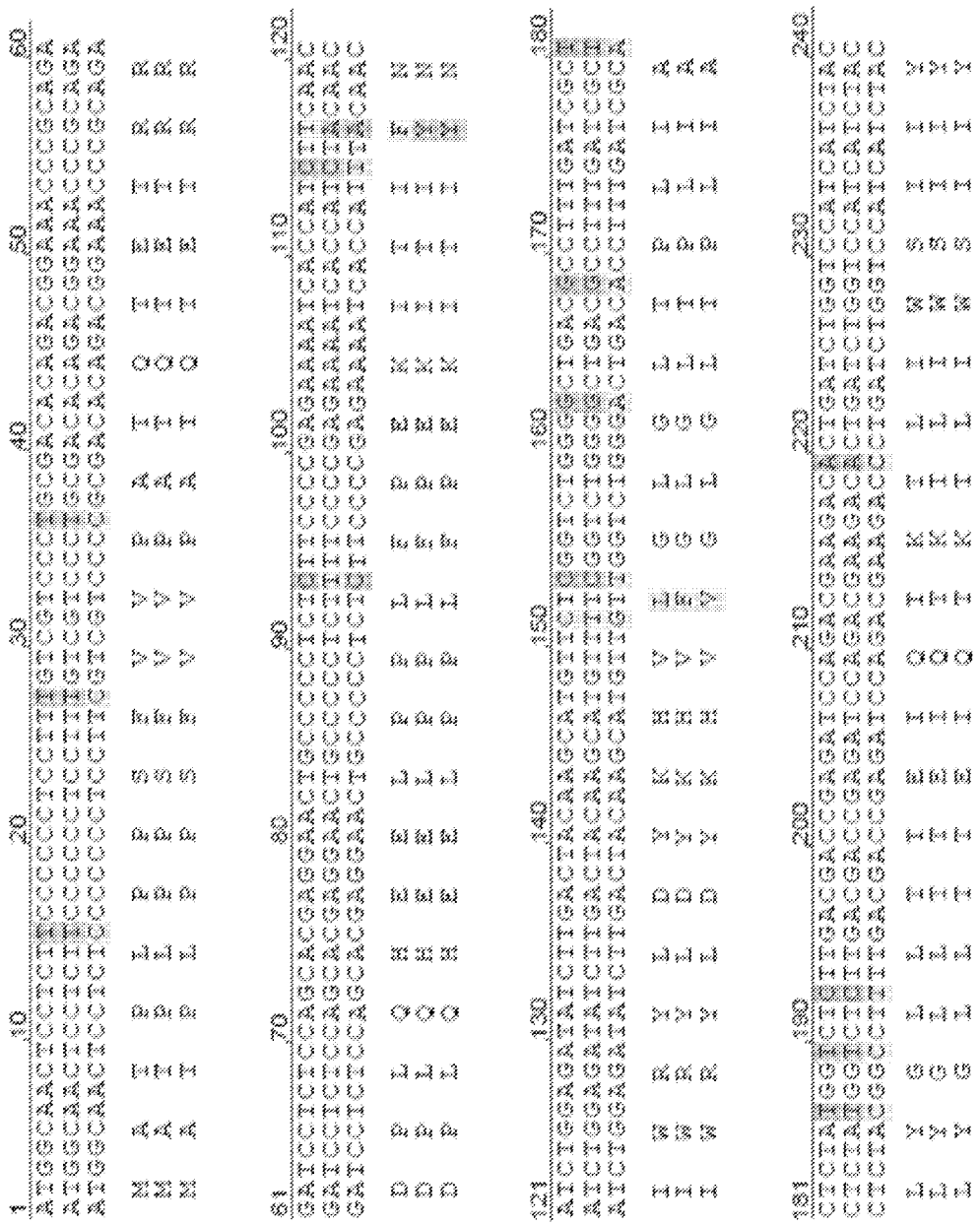
Figure 2B:
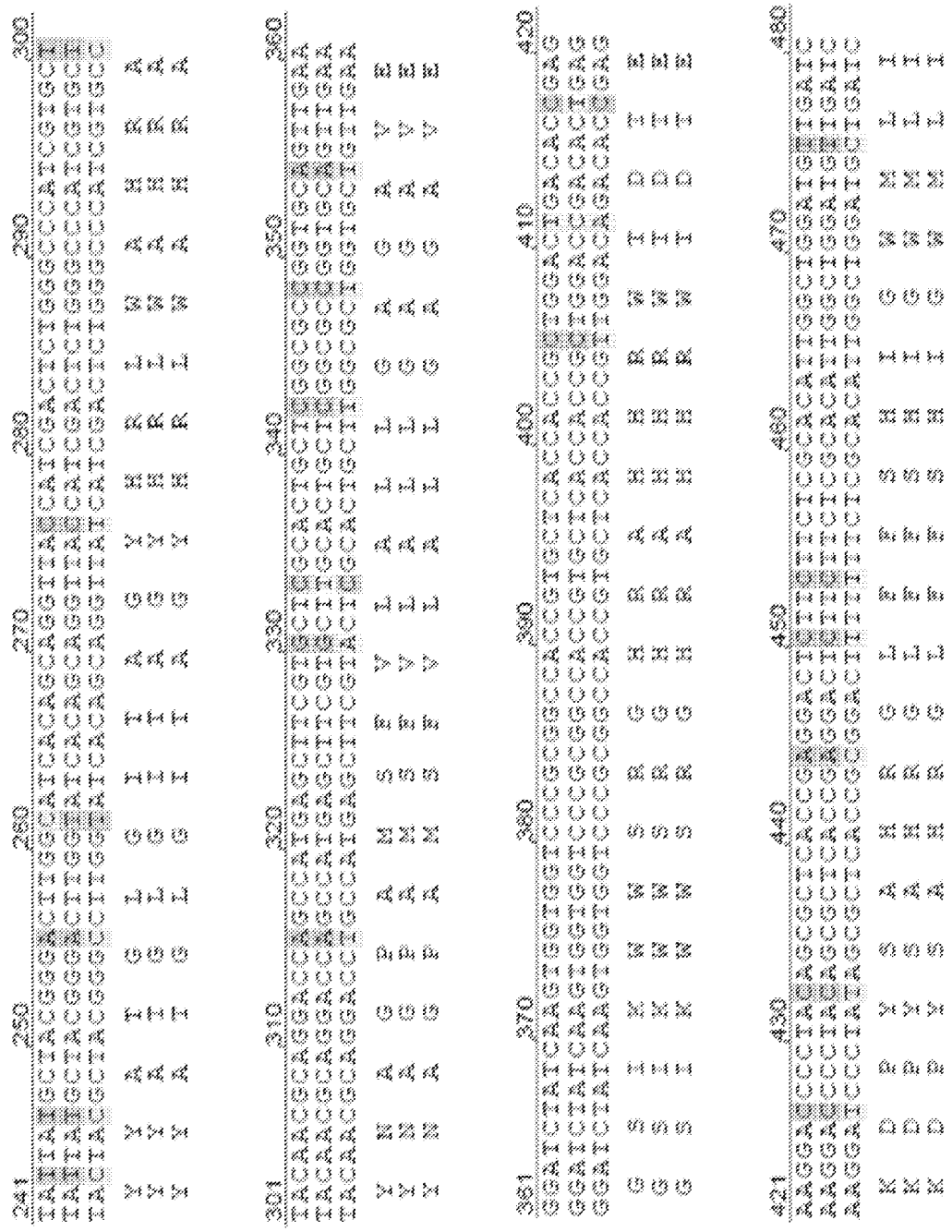
Figure 2C:
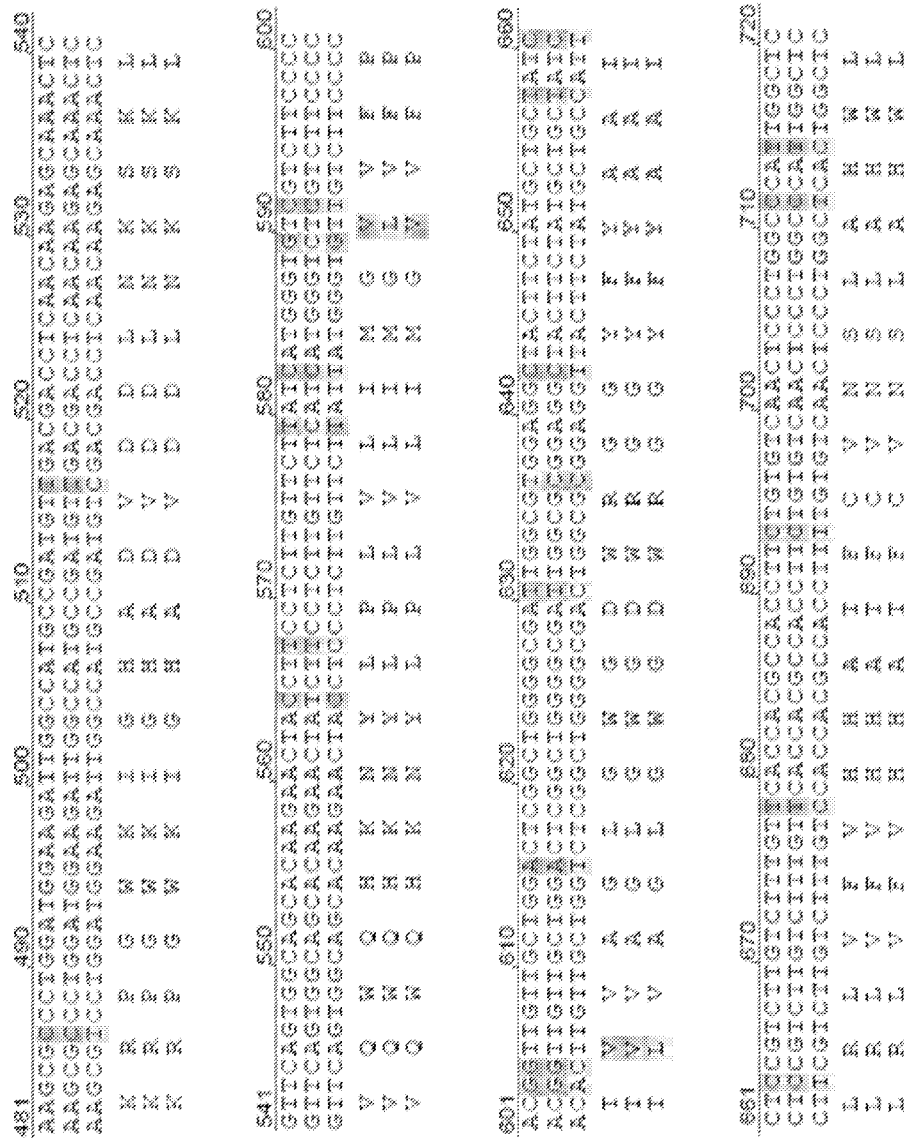
Figure 2E:
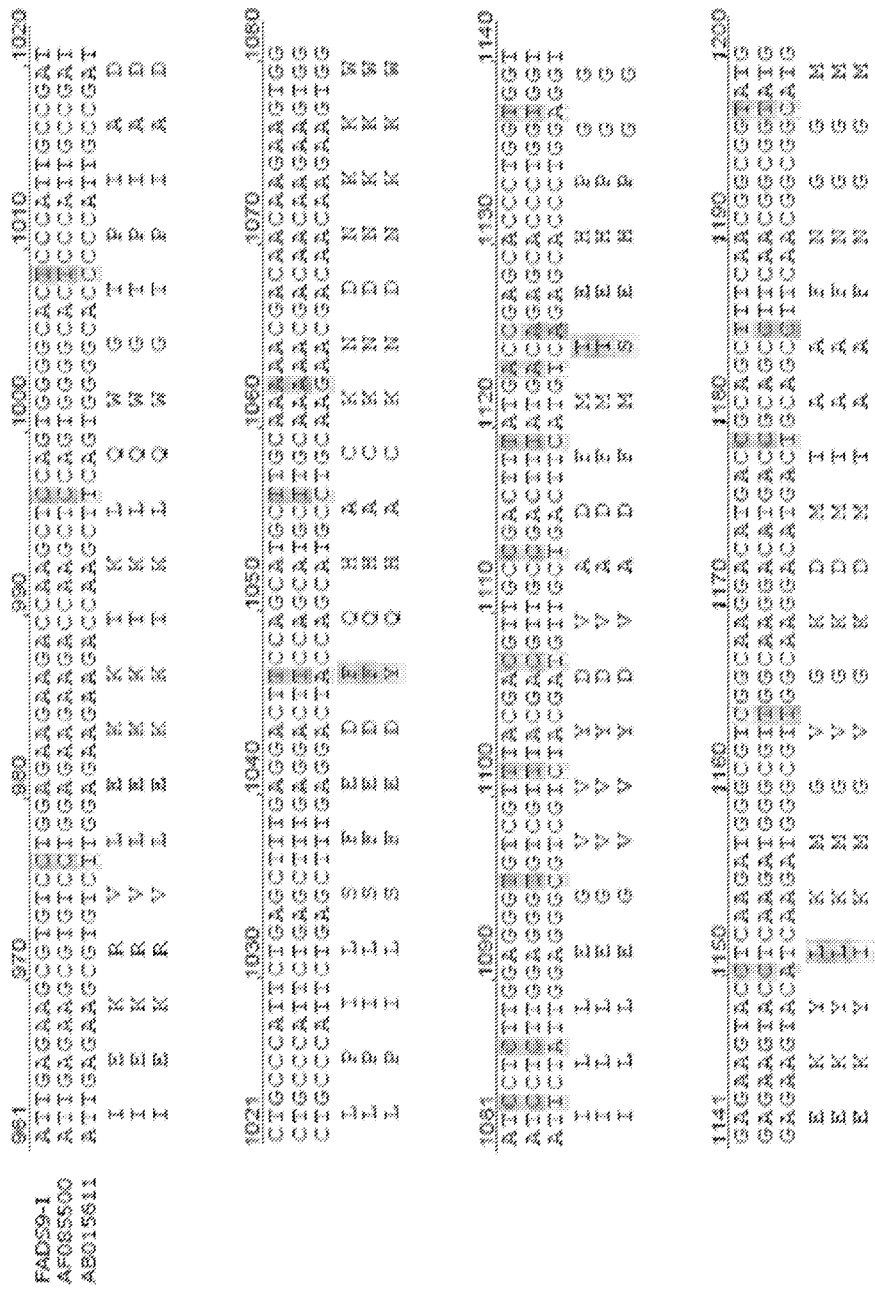
Figure 2F:
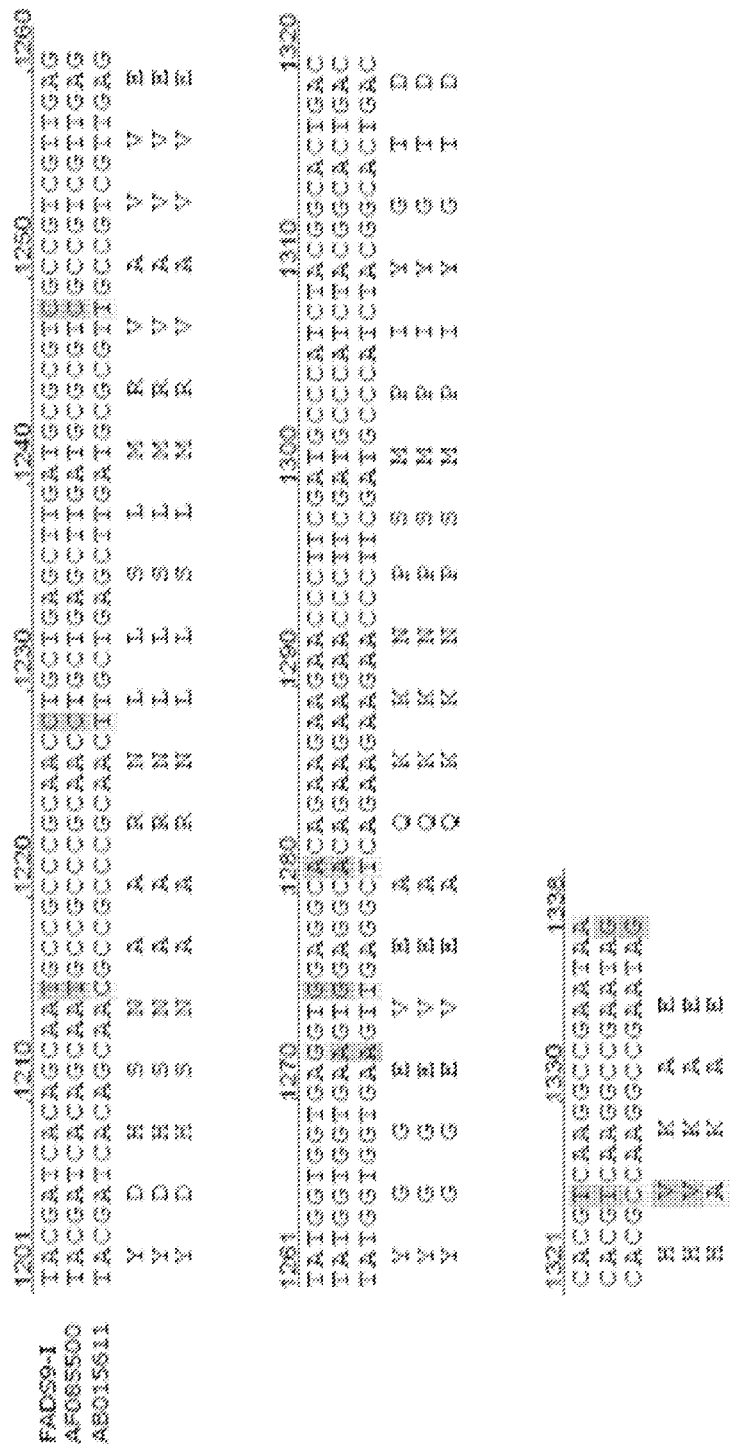
Figure 3B:
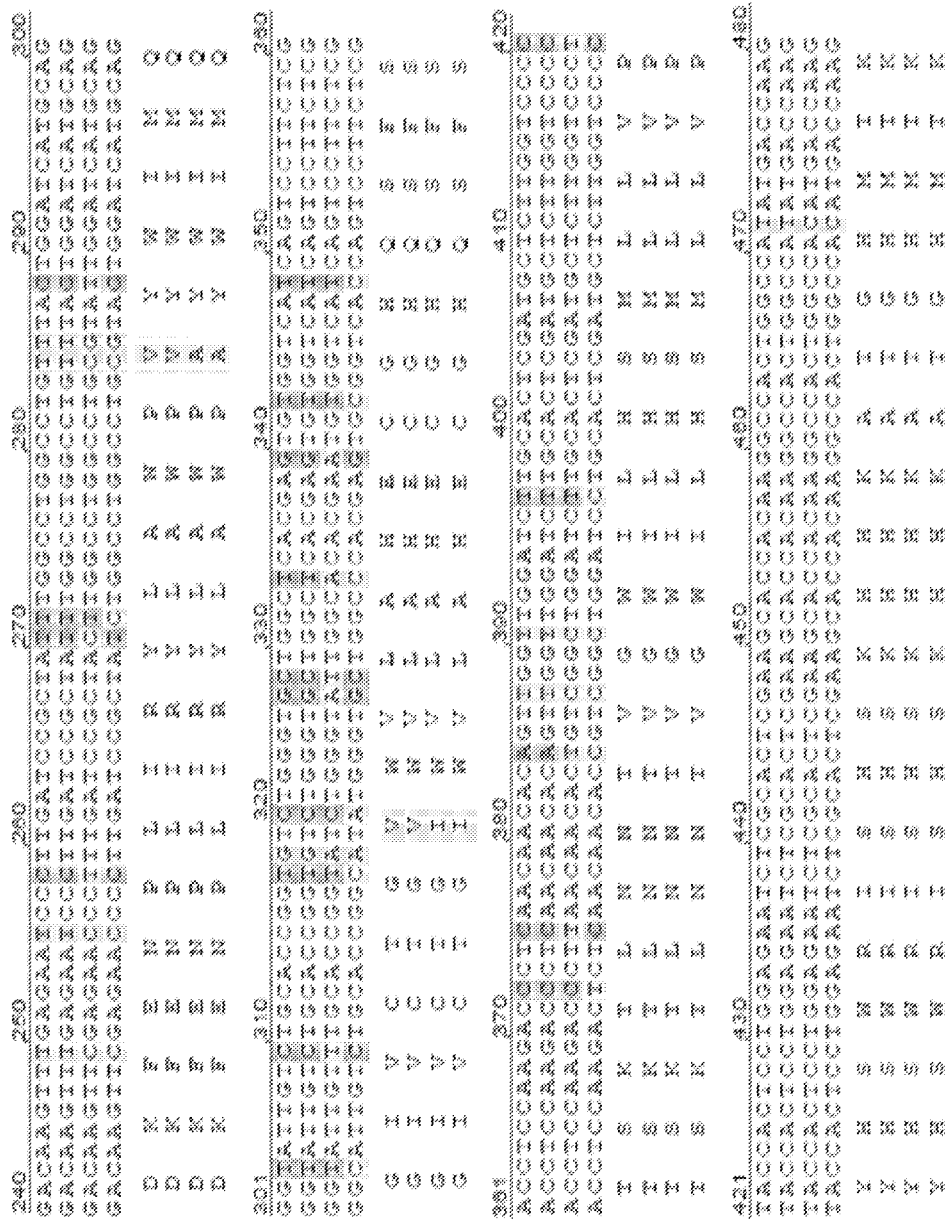
Figure 3C:
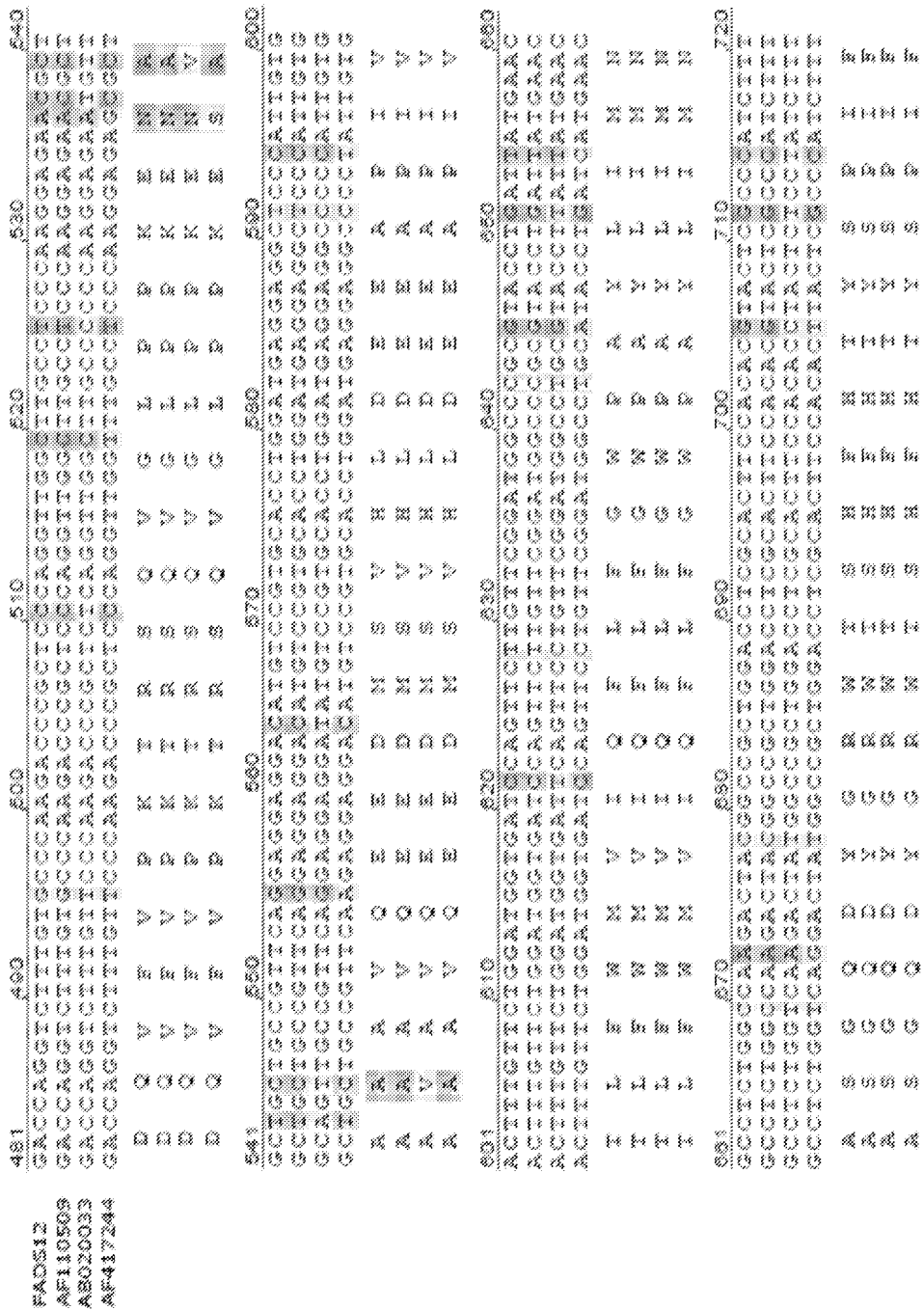
Figure 3D:
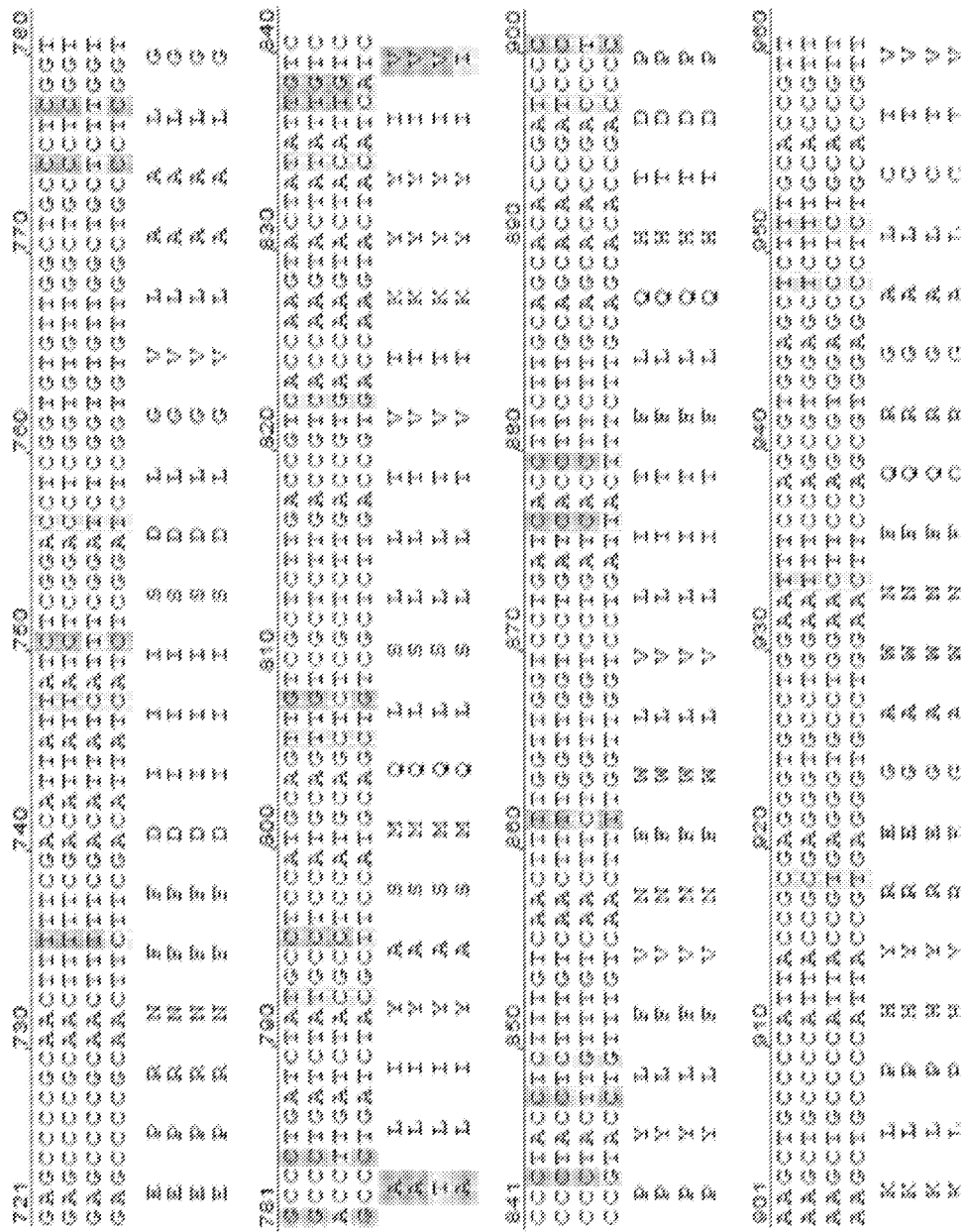
Figure 3E:
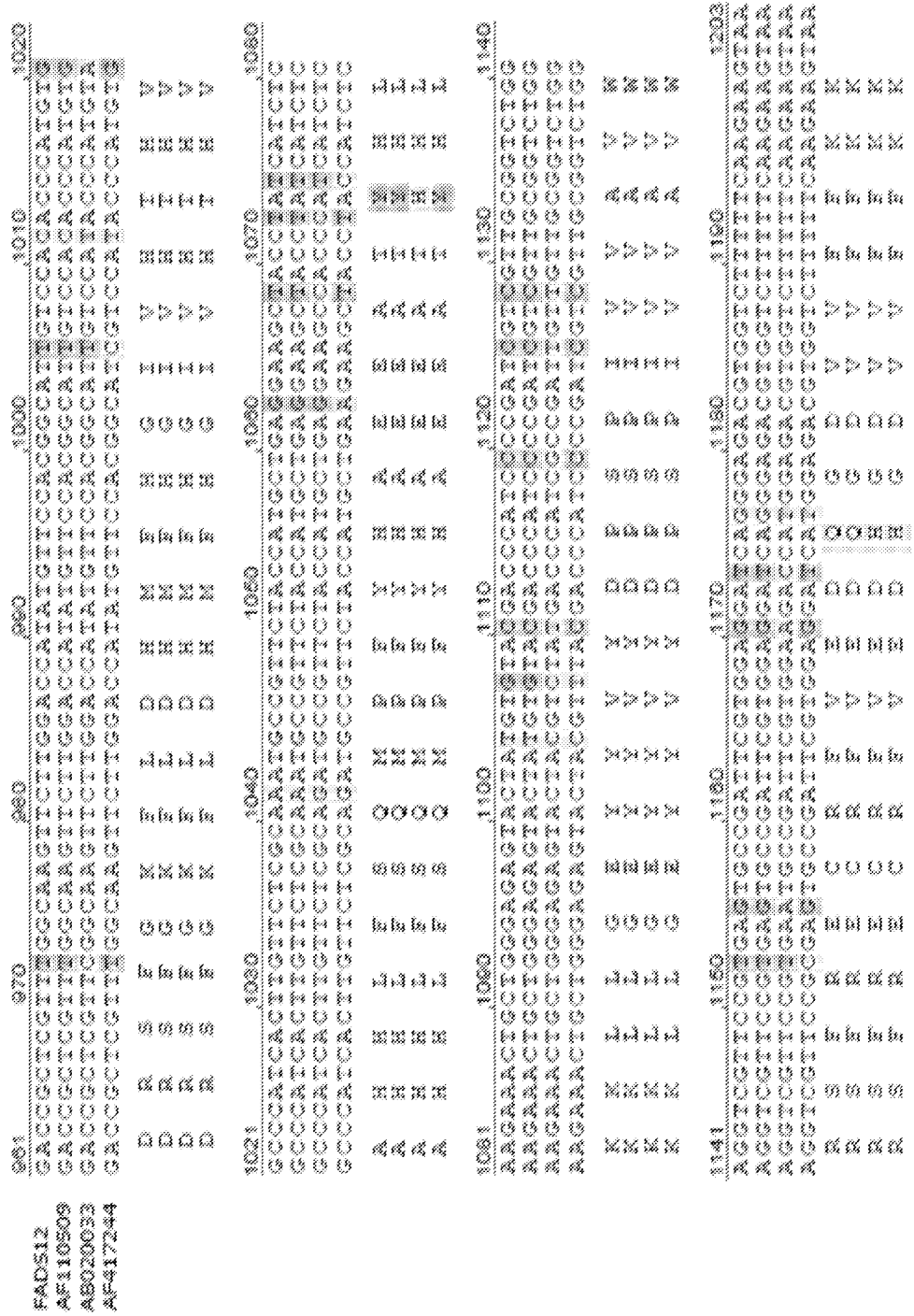
Figure 4A:
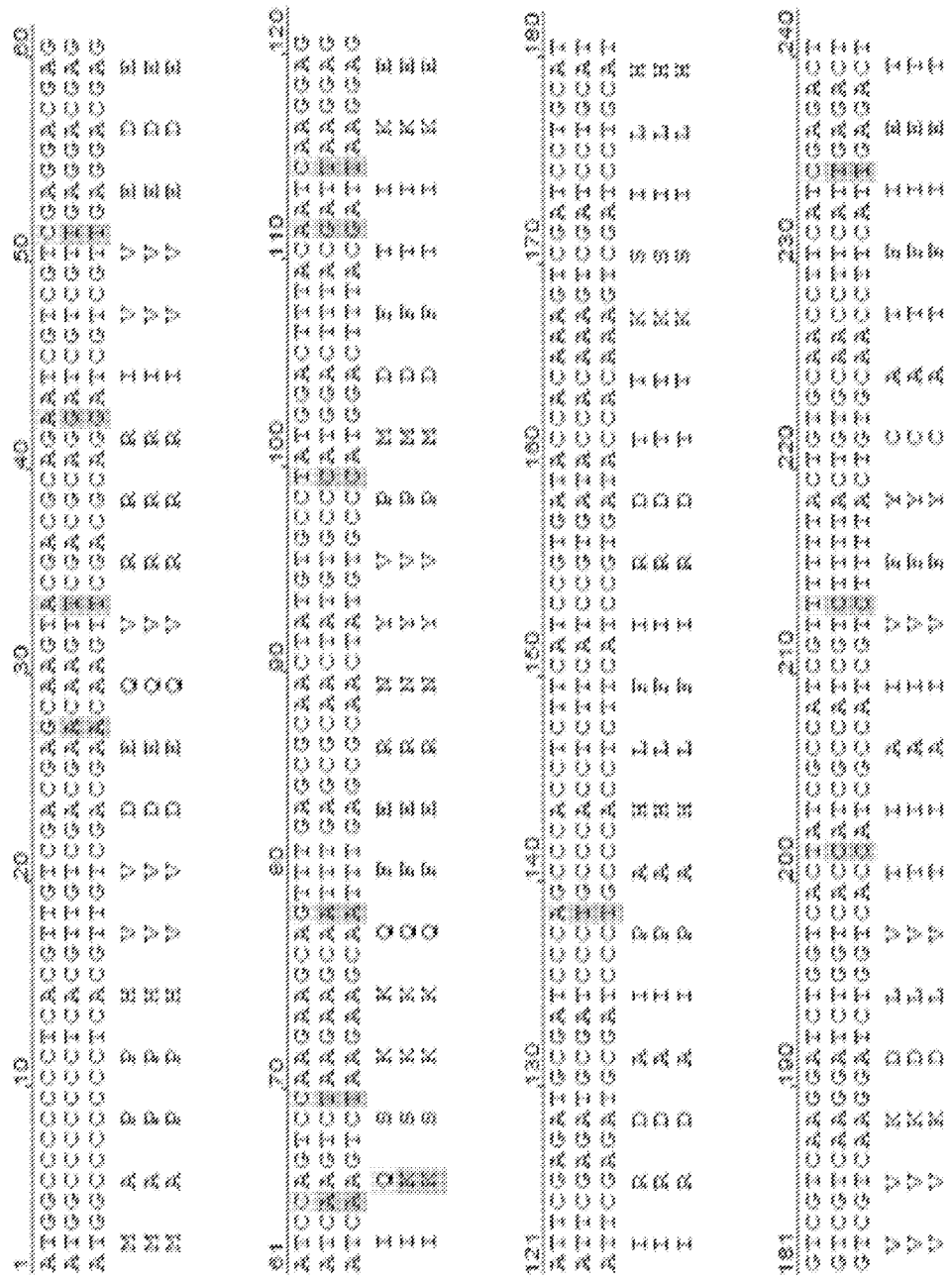
Figure 4B:
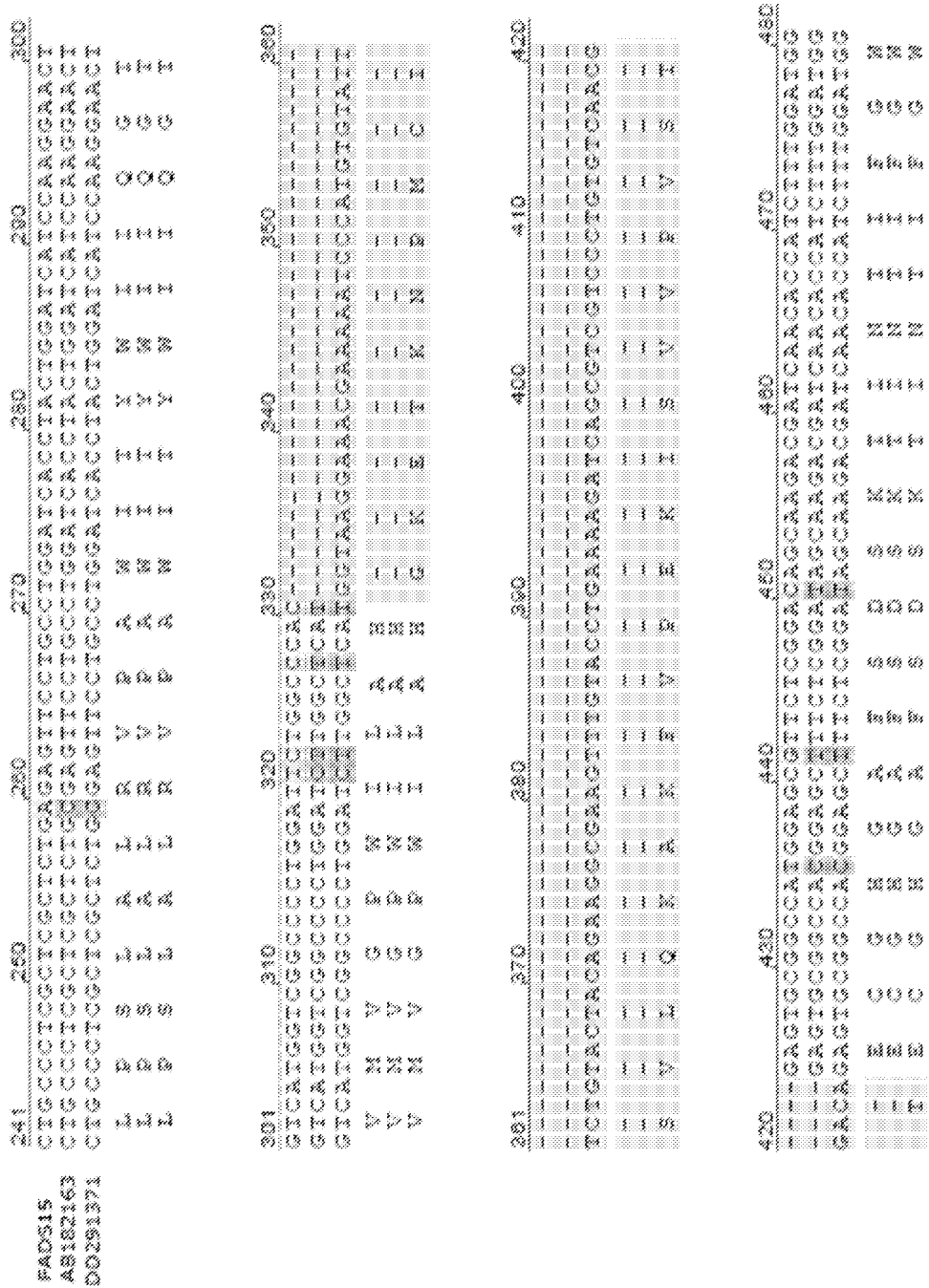
Figure 4C:
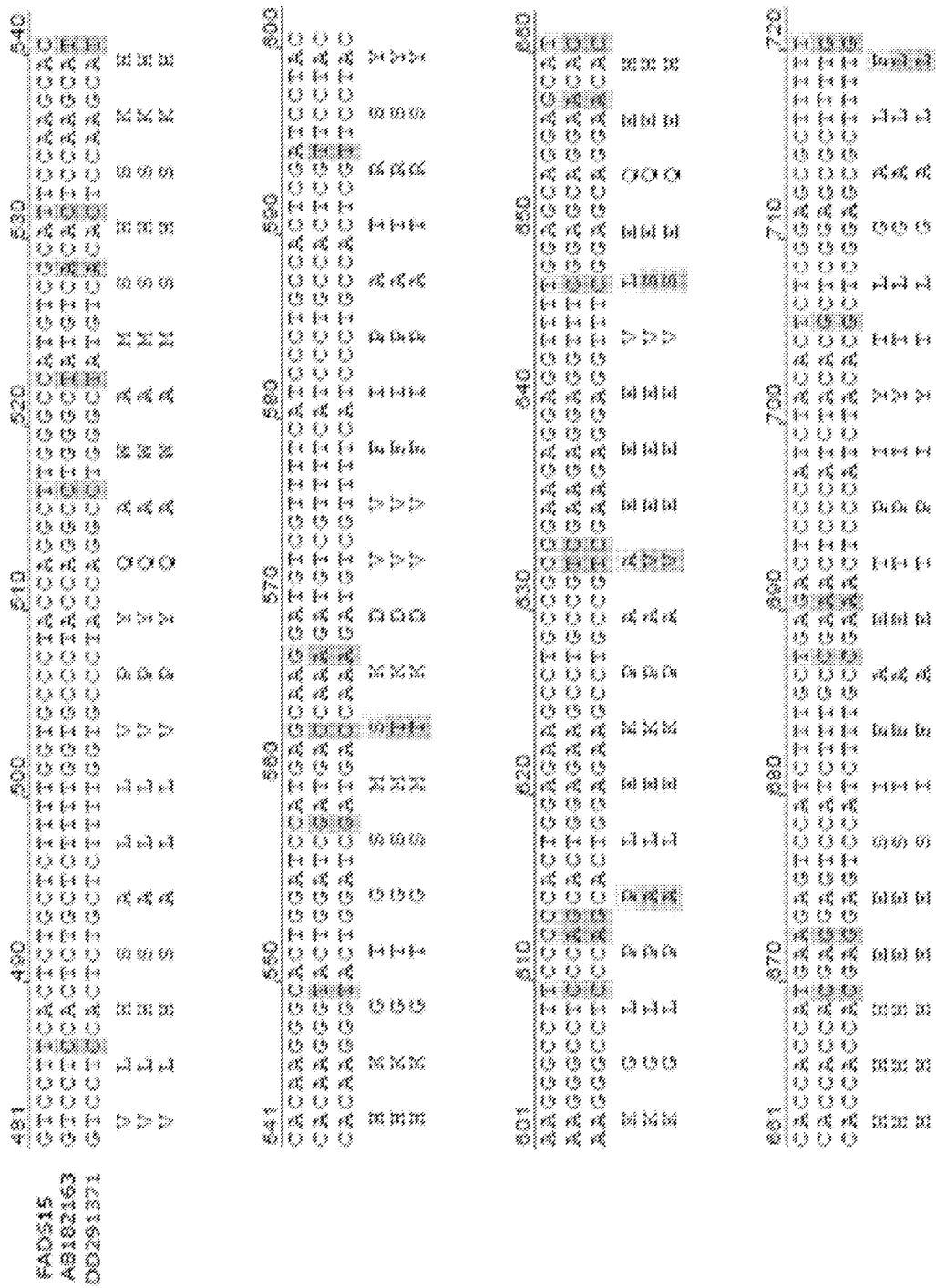
Figure 4D:
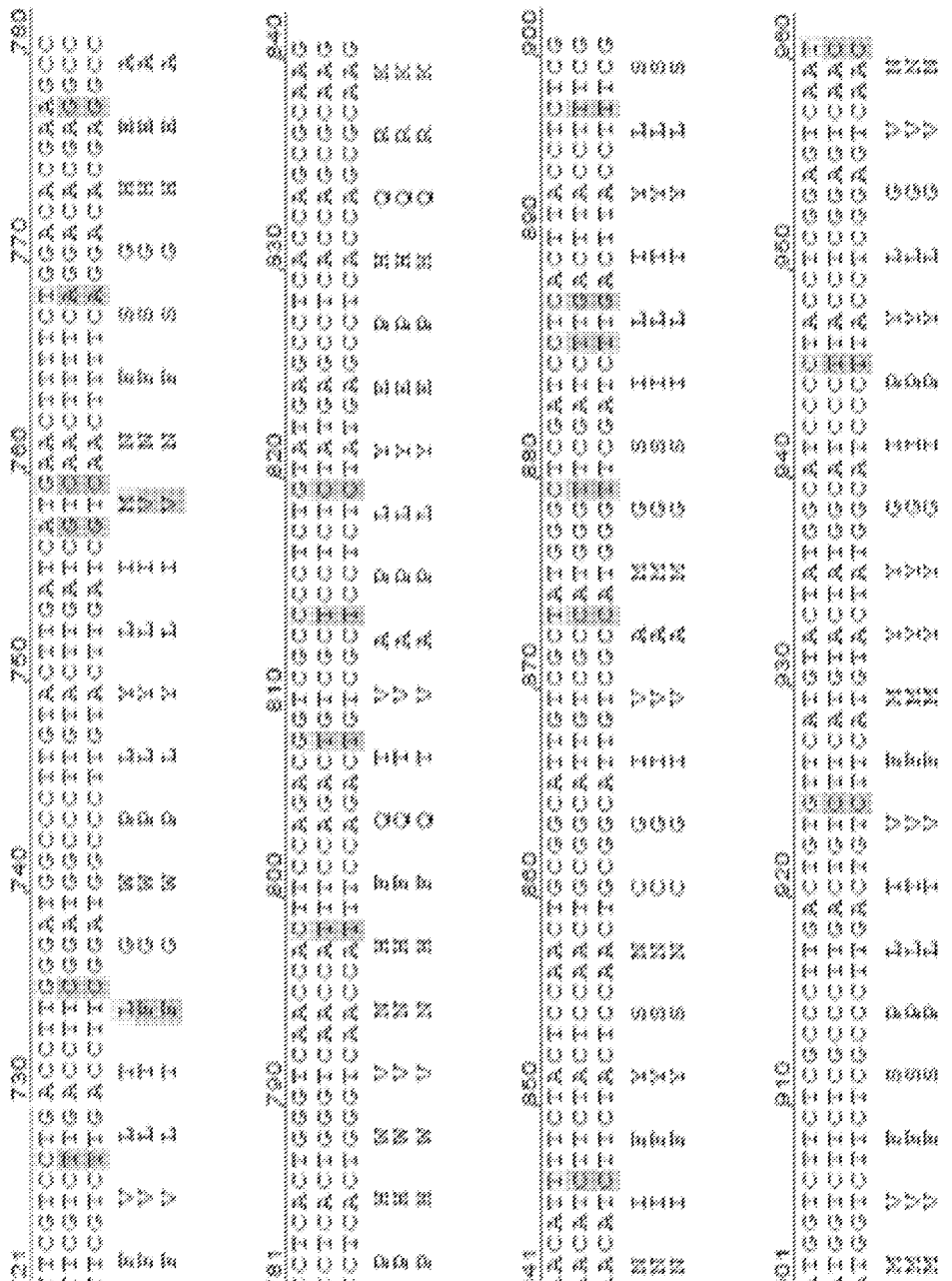
Figure 4E:
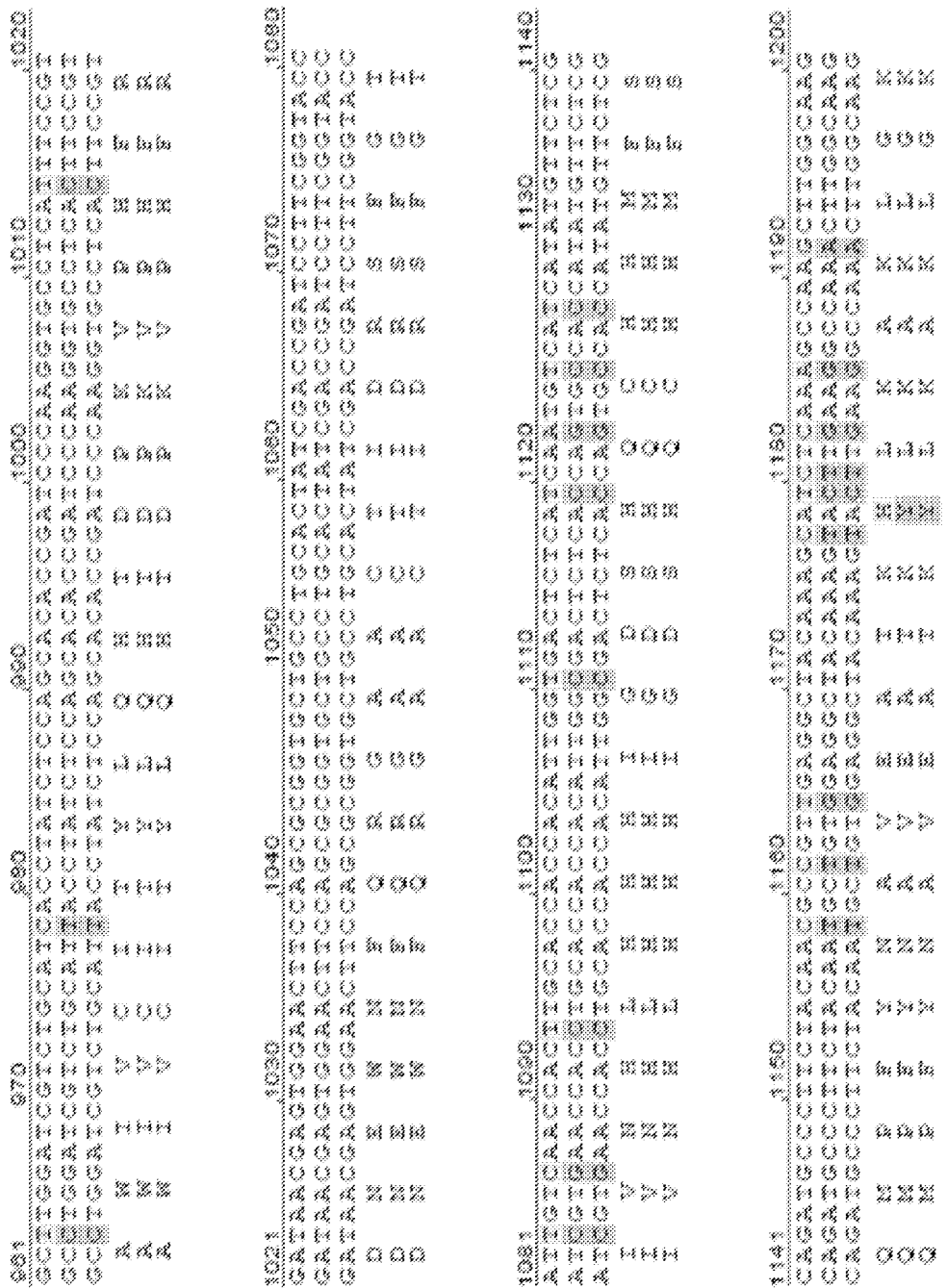
Figure 4F:
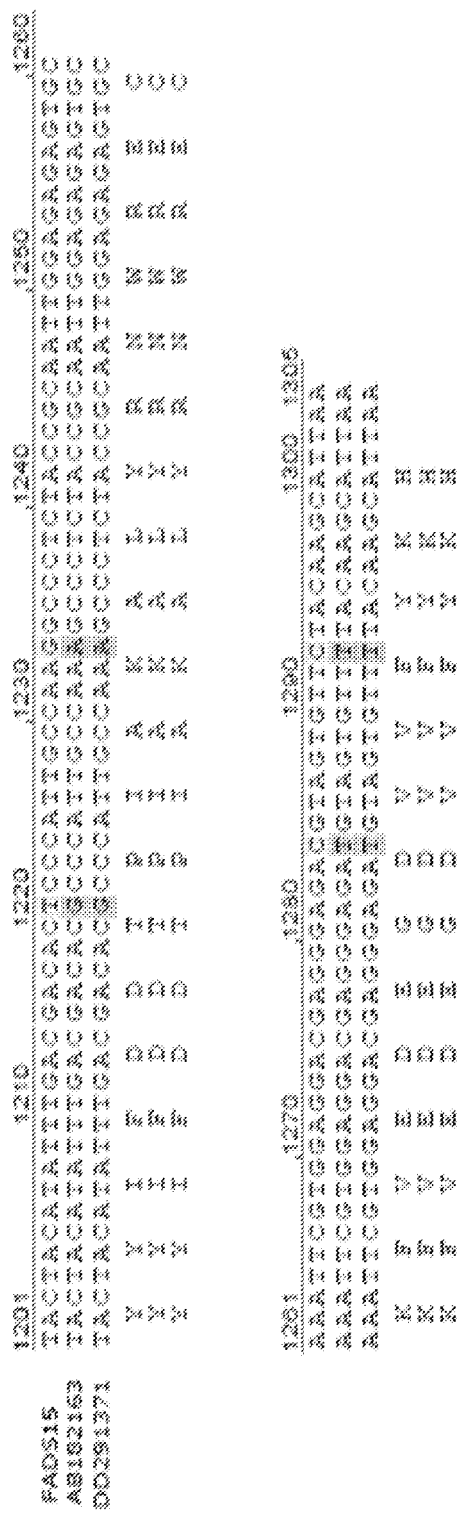

FATTY ACID DESATURASE USED IN THE BIOSYNTHESIS OF LONG CHAIN OMEGA-3 POLYUNSATURATED FATTY ACIDS

This application claims priority to U.S. patent application Ser. No. 13/646,667 filed 6 Oct. 2012 which claimed priority to Chinese Patent Application Ser. No. 201210309215.2 filed 29 Aug. 2012.

FIELD OF INVENTION

The present invention relates to the field of microbial manufacturing of polyunsaturated fatty acids (PUFAs), specifically to the fatty acid desaturases in the synthesis process of polyunsaturated fatty acids.

BACKGROUND OF THE INVENTION

Lipids are first synthesized as saturated fatty acids and double bonds are introduced post-synthetically by oxygen-dependent enzymes known as fatty acid desaturases, in a process that is initiated by abstraction of hydrogen from a methylene group. Fatty acid desaturases are divided into soluble and integral membrane classes, which may have been evolved independently (Shanklin J, Somerville C., "Stearoyl-acyl-carrier-protein desaturase from higher plants is structurally unrelated to the animal and fungal homologs", Proc Natl Acad Sci USA 1991; 88:2510-4). The acyl-ACP desaturases are soluble enzymes found in the plastids of higher plants, whereas the more widespread class of integral membrane acyl-CoA desaturases is found in endomembrane systems in prokaryotes and eukaryotes (Shanklin J, Cahoon E B., "Desaturation and Related Modifications of Fatty Acids1", Annu Rev Plant Physiol Plant Mol Biol 1998; 49:611-41). Fatty acid desaturases in each class are closely related homologs based on their amino acid sequences, and yet perform highly regio- and stereo-selective reactions on long-chain fatty acids composed of essentially equivalent methylene chains that lack distinguishing landmarks close to the site of desaturation. As pointed out by Nobel Laureate Dr. Konrad Bloch, this region- and stereo-specific removal of hydrogen "would seem to approach the limits of the discriminatory power of enzymes" (Bloch K., "Enzymatic synthesis of monounsaturated fatty acids", Accounts of Chemical Research 1969; 2:193-202).

The membrane class of desaturases consists of enzymes with c5, c6, c9, c12 or ω3 regio-selectivity. Mammalian cells possess c5, c6 and c9, but lack c12 and ω3 desaturases (Berquin I M, Edwards I J, Kridel S J, Chen Y Q, "Polyunsaturated fatty acid metabolism in prostate cancer", Cancer Metastasis Rev 2011; 30:295-309, and Chen Y Q, Edwards I J, Kridel S J, Thornburg T, Berquin I M., "Dietary fat-gene interactions in cancer", Cancer Metastasis Rev 2007; 26:535-51). *Mortierella alpina* belongs to the subphylum of *Mucoromycotina* (Hibbett D S, Binder M, Bischoff J F, et al., "A higher-level phylogenetic classification of the Fungi", Mycol Res 2007; 111:509-47). It can produce lipids up to 50% of its dry weight. We have recently characterized *M. alpina* genome (Wang L, Chen W, Feng Y, et al., "Genome Characterization of the Oleaginous Fungus *Mortierella* alpine", PLoS One 2011; 6:e28319) which encodes one c5, two c6, three c9, one c12 and one ω3 desaturase. Therefore, *M. alpina* has all known regio-selective groups of membrane desaturases.

We have expressed *M. alpina* c9, c12 and ω3 desaturases (FADS9-I, FADS12 and FADS15) in the methylotrophic yeast *Pichia pastoris*, purified the recombinant proteins and determined their enzymatic activities.

DETAILED DESCRIPTION OF THE INVENTION

The applicant has identified a novel ω3 desaturase and a Δ9 desaturase, successfully expressed, purified and characterized their enzymatic activities More specifically, the applicant designed primers of nucleotide aiming to three desaturases coding for Δ9-I Des, Δ12 Des and ω3 Des on the basis of whole-genome sequencing of *M. alpina*, the sequences of specific primers are listed in Table 1. *M. alpina* RNA was extracted and reverse transcribed to obtain cDNA. The amplified three sequences by PCR with three pairs of primer of FF1 and FR1, FF2 and FR2, FF3 and FR3 to PCR were inserted into pET19b (PP) and sequenced, and then subcloned into pPinkα-HC, an expression vector in *Pichia pastoris*. Expression vectors were linearized and transformed into PichiaPink strain 2. The recombinant strains thus obtained express the above-mentioned three desaturases. The enzyme activity analysis showed that the purified recombinant desaturases were functional The present invention provides genes coding for *M. alpina* ω3 desaturase (FADS15) and Δ9 desaturase (FADS9-I), whose nucleic acid sequences are shown as SEQ ID NO:1 and SEQ ID NO:3, respectively.

The present invention also provides expression vectors respectively containing SEQ ID NO:1 and SEQ ID NO:3 which can respectively express *M. alpina* ω3 desaturase (FADS15) and Δ9 desaturase (FADS9-I). Preferably, the said expression vector is *Pichia pastoris* expression vector.

The present invention also provides a recombinant microorganism which can respectively express ω3 desaturase (FADS15) and *M. alpina* Δ9 desaturase (FADS9-I). Preferably, the said recombinant microorganism is recombinant *Pichia pastoris* PichiaPink strain 2, which contains *Pichia pastoris* expression vector carrying SEQ ID NO:1 or SEQ ID NO:3.

The present invention successfully expresses and purifies the novel membrane ω3 desaturase (FADS15) and Δ9 desaturase (FADS9-I), which play a key role in the polyunsaturated fatty acid biosynthetic pathway, and whose amino acid sequences are shown as SEQ ID NO:2 and SEQ ID NO:4. Furthermore, the present invention verifies the enzyme activity of the above two kinds of membrane desaturases. The present invention apply the above-mentioned novel membrane desaturases ω3 desaturase (FADS15) in the polyunsaturated fatty acid biosynthesis, converting fatty acid $C18:1^{\Delta 9}$ into $C18:2^{\Delta 9,15}$, $C18:2^{\Delta 9,12}$ into $C18:3^{\Delta 9,12,15}$, $C20:4^{\Delta 5,8,11,14}$ into $C20:5^{\Delta 5,8,11,14,17}$. Omega-3 polyunsaturated fatty acids can be utilized as food supplementation to prevent human disorders, wherein said human disorders consisting of cancer, cardiovascular disease, inflammation, developmental disorders, psychiatric disorders, and cognitive aging.

TABLE 1

Primers' sequence table and its restriction enzyme cutting site:

| Name | Sequence | Targeted vector |
| --- | --- | --- |
| FF1 (SEQ ID: 5) | atat*CATATG*ATGGCCCCCCCTC ACGTTGTCGACGAGCA(Nde I) | pET19b-FADS15 |
| FF2 (SEQ ID: 6) | atat*ATTAAT*ATGGCACCTCCCA ACACTATTGATGCCGG(Ase I) | pET19b-FADS12 |

TABLE 1-continued

Primers' sequence table and its restriction enzyme cutting site:

| Name | Sequence | Targeted vector |
|---|---|---|
| FF3 (SEQ ID: 7) | atat_CATATG_ATGGCAACTCCTC TTCCCCCCTCCTTTGT (Nde I) | pET19b-FADS9-I |
| FR1 (SEQ ID: 8) | atat_GGATCC_TAATGCTTGTAG AACACTACGTC (BamH I) | pET19b-FADS15 |
| FR2 (SEQ ID: 9) | atat_GGATCC_TTACTTCTTGA AAAAGACCACGTC (BamH I) | pET19b-FADS12 |
| FR3 (SEQ ID: 10) | atat_AGATCT_TTATTCGGCCT TGACGTGGTCAGT (BgI II) | pET19b-FADS9-I |
| SF1 (SEQ ID: 11) | atatat TGCGCACATCATCAT CATCATCATCAT (Fsp I) | pPink-FADS |
| SR1 (SEQ ID: 12) | atat_GAATTC_AT_ATTTAAAT T_ AATGCTTGTAGAACACTACGTC (Eco RI, Swa I) | pPink-FADS15 |
| SR2 (SEQ ID: 13) | atatat_GGTACC_TTACTTCT TGAAAAAGACCACGTC (Kpn I) | pPink-FADS12 |
| SR3 (SEQ ID: 14) | atatat_GGTACC_TTATTCGGCC TTGACGTGGTCAGT (Kpn I) | pPink-FADS9-I |

DESCRIPTION OF THE ATTACHED DRAWINGS

FIG. 1: Diagram of the cloning strategy for desaturase expression vectors. FADS coding sequences were PCR amplified using primers listed in Table 1. PCR fragment were digested with indicated restriction enzymes, column purified and inserted into the pET-19b(PP) vector linearized with corresponding restriction enzymes. The FADS coding sequence plus His tag and Precision protease recognition sequence were PCR amplified and inserted into the pPinkalpha-HC vector. TRP2: TRP2 gene, AmpR: ampicillin resistance gene, pUC ori: oriental promoter of pUC, PAOX1: 5'AOX1 promoter region, α-factor: α-mating factor secretion signal, CYC1 TT: CCY1 transcription termination region, PADE2 HC: high-copy ADE2 promoter region, ADE2: ADE2 open reading frame.

FIG. 2A-F: the sequencing results of the clone sequence of ω3 desaturase (FADS15), in which FADS15 nucleotide sequence from _M. alpina_ ATCC#32222 shows 93.1% identity with AB182163 from _M. alpina_ 1s-4.

FIG. 3A-E: the sequencing results of the clone sequence of Δ12 desaturase (FADS12), in which FADS12 nucleotide sequence from _M. alpina_ ATCC#32222 shows 99.9% identity with AF110509 from _M. alpina_ 1s-4.

FIG. 4A-F: the sequencing results of the clone sequence of Δ9 desaturase (FADS9-I), in which FADS9-I nucleotide sequence from _M. alpina_ ATCC#32222 shows 98.4% identity with AF085500 from _M. alpina_ 1s-4.

Figures 5A, 5B:
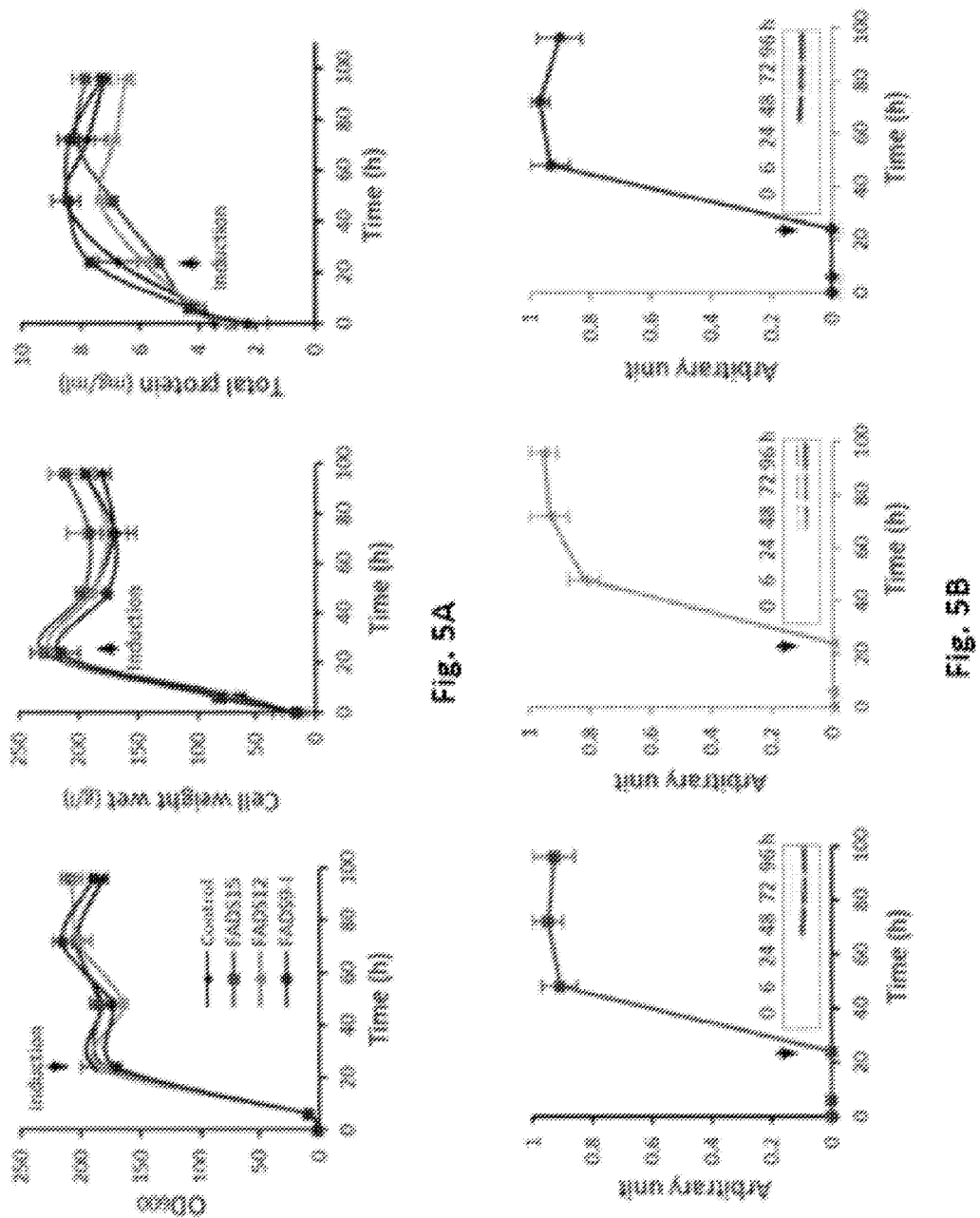

FIG. 5A: Growth curve of the recombinant _P. pastoris_ measured by cell density, wet weight and total protein concentration.

FIG. 5B: Kinetics of recombinant protein induction. Desaturase expression was determined by Western blotting using anti-His tag antibody. The normalized level of highest expression was set at one arbitrary unit. Three independent experiments were performed and bars represent standard deviations.

Figure 5C:
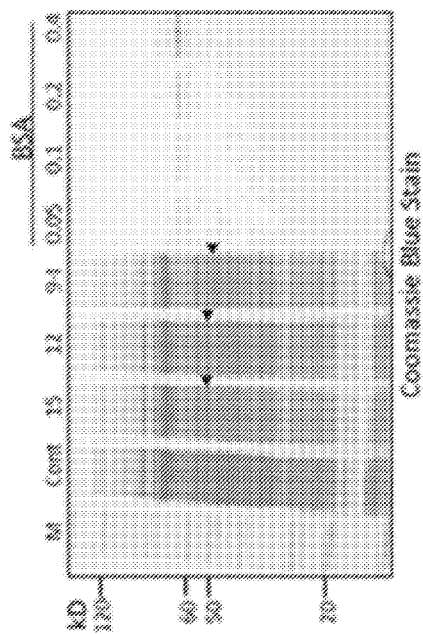

FIG. 5C: Quantification of the recombinant desaturase proteins by Coomassie blue staining after SDS-PAGE. Known concentrations of BSA were used as quantification standard.

Figure 5D:
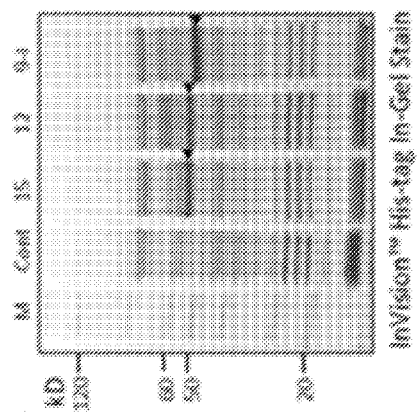

FIG. 5D: InVision™ His-tag In-Gel Stain of recombinant FADS proteins. The arrow head indicates the addition of methanol for induction of recombinant protein expression. The triangles indicate the expressed recombinant proteins. M: protein marker, Cont: negative control which was PichiaPink™ harboring pPinkα-HC, 15: FADS15, 12: FADS12, 9-I: FADS9-I.

FIG. 6A: Fractionation of recombinant desaturases. InVision™ His-tag In-Gel Staining after SDS-PAGE analysis of FADS9-I membrane (top panel) and supernatant fraction (bottom panel), using different speeds of centrifugation. The triangles indicate the recombinant FADS9-I.

Figure 6B:
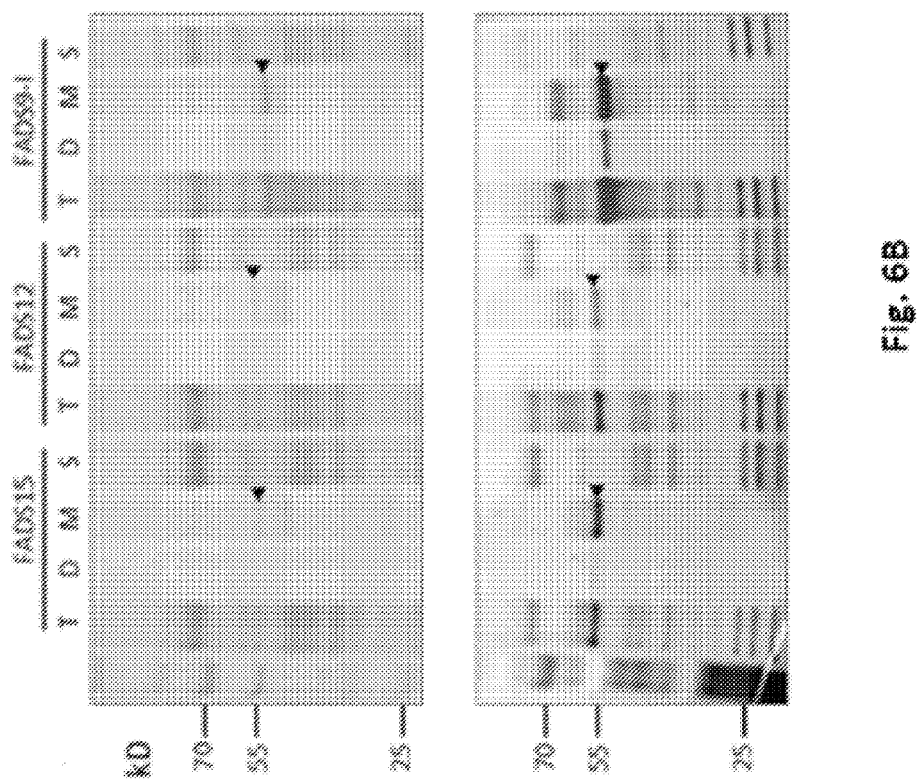

FIG. 6B: Coomassie blue Staining and InVision™ His-tag In-Gel Staining of recombinant desaturases after fractionation. T: total protein after grinded by glass beads, D: debris after centrifugation at 500 g for 10 min, M: membrane fraction after centrifugation at 10,000 g for 10 min, S: supernatant after the centrifugation. The triangles indicate the recombinant desaturase proteins.

Figure 7A:
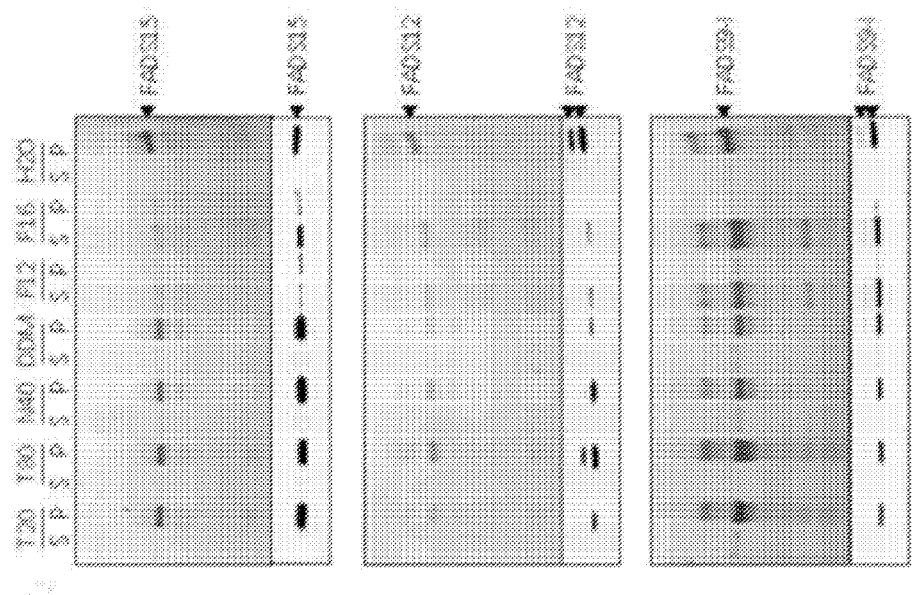

FIG. 7A: Solubilization of recombinant desaturases. Membrane fractions were suspended in 1% concentrations of various detergents and incubated at 4° C. for 2 hr. Proteins were visualized by InVision™ His-tag In-Gel Staining (upper panel) and Western blot (lower panel). T20: Tween-20, T80: Tween-80, N40: NP-40, DDM: n-Dodecyl-β-D-maltoside, F12: Fos-Choline 12, F16: Fos-Choline 16,S: supernatant, P: pellet.

Figure 7B:
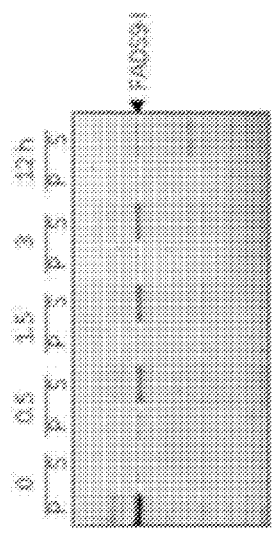

FIG. 7B: Membrane fractions of recombinant FADS9-I were suspended in 1% Fos-Choline 16 and incubated at 4° C. for various time (0, 0.5, 1.5, 3, 12 hr). Aliquots were analyzed by InVision™ His-tag In-Gel Staining. S: supernatant, P: pellet.

Figure 7C:
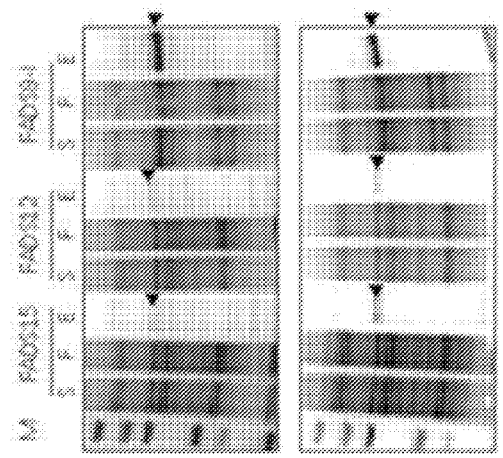

FIG. 7C: One-step purification using His Mag Sepharose Ni beads under the high yield (upper panel) and high stringency conditions (lower panel). Proteins were analyzed by SDS-PAGE and Coomassie blue staining. M: protein marker, S: supernatant, F: flow through, E: eluate.

SPECIFIC EMBODIMENTS

Example 1

_Mortierella alpina_ Culture

_Mortierella alpina_ (#32222, American Type Culture Collection, Manassas, Va., USA) was inoculated on Potato Dextrose Agar (PDA) plates (BD Difco™ Potato Dextrose Agar cat#213400) and incubated for 20-30 days at 25° C. 5 mL broth (20 g/L Glucose, 5 g/L Bacto yeast extract BD Biosciences cat#212750, 1 g/L $KH_2PO_4$, 0.25 g/L $MgSO_4$, 10 g/L $KNO_3$) were added to three plates. Spores were gently scraped off the surface with a sterile loop, and then filtrated through a 40 micron cell strainer. Spores were concentrated by centrifuging at 12,000×g for 15 min, suspended in a small volume of broth, enumerated using a hemocytometer, and kept at −80° C. in 30% glycerol at a density of approximately $10^7$ spores/mL. Alternatively, 3 mL of unconcentrated spore suspension were directly added into 45 mL broth without $KNO_3$ in a 250-mL flask covered with 8 layers of cheese cloth, and shaken at 200 rpm, 25° C. for 5 days. Cultures were blended using a Braun hand blender for 5 sec/pulse, 8 pulses, then 0.3 g wet mycelia were inoculated into 45 mL broth without $KNO_3$ in a 250-ml flask and shaken at 200 rpm, 25° C. for 24 h. The above step was repeated once, by which time the whole fungal culture was in proliferative phase and ready for experiments. Mycelia were collected by filtration and weighed. Samples were snap-frozen in liquid nitrogen, pulverized and kept at −80° C. for RNA extraction.

Example 2

Expression Vector Construction

*M. alpina* RNA extraction was performed using Trizol Reagent (Invitrogen, CA) according to the manufacturer's instructions. Total RNA was reverse transcribed with SuperScript® III First-Strand Synthesis SuperMix (Invitrogen) following the manufacturer's instructions. Using both C- and N-terminal sequences as primers (Table 1), desaturase coding sequences were PCR amplified as follows: denaturation at 95° C. for 30 sec, annealing at 55° C. for 45 sec and extension at 72° C. for 1 min for 25 cycles. The amplified products were cloned into a modified pET19 vector (Novagen) derivative containing a PreScission protease cleavage site (GE Healthcare) between the multiple cloning site and N-terminal His tag (Jonsson T J, Johnson L C, Lowther W T (2009) Protein engineering of the quaternary sulfuredoxin.peroxiredoxin enzyme.substrate complex reveals the molecular basis for cysteine sulfinic acid phosphorylation. J Biol Chem 284: 33305-33310.) to construct pET19b-FADS15, pET19b-FADS12 and pET19b-FADS9-I). The desaturase genes, including the His-Tag and PreScission protease cleavage site, were then PCR amplified using primers SF1 and SR1-SR3 (Table 1). The PCR conditions used were the same as the first step for cDNAs. The PCR fragments were then purified and inserted into pPinkα-HC to generate the expression vectors pPinkα-HC-FADS15, pPinkα-HC-FADS12 and pPinkα-HC-FADS9-I. The presence of the inserts in the plasmids was confirmed by restriction digestion analysis and sequencing. The strategy used for constructing desaturase expression vectors is shown in FIG. 1. Sequencing results from the amplified fragment of these desaturases are in FIG. 2-4. The FADS12 and FADS9-I genes from *M. alpina* ATCC#32222 are 99.9% and 98.4% identical, respectively, to the corresponding genes from *M. alpina* 1s-4. The FADS12 and FADS9-I proteins from *M. alpina* ATCC#32222 are 100% and 99.6% identical, respectively, to these proteins from *M. alpina* 1s-4. The high similarity of FADS12 and FADS9-I genes between two strains indicates that these genes are highly conserved in *M. alpina*. Interestingly, the FADS15 gene is much less conserved at both DNA (93.1% identity) and protein (97.9%) levels.

Example 3

Protein Expression

Desaturase expression vectors and pPinkα-HC (negative control vector) were linearized with restriction enzyme Spe I and transformed into *P. pastoris* strains (PichiaPink strain 1, 2, 3 and 4) using the MicroPulser Electroporator (Bio-Rad Laboratories, Hercules, Calif.) according to the User Manual of PichiaPink Expression System (Invitrogen). *P. pastoris* were incubated with YPDS media (YPD with 1 M sorbitol) in the Gene Pulser Cuvettes at 28° C. for 2 hr without shaking, spread onto PAD (Pichia Adenine Dropout) agar selection plates, and then incubated at 28° C. for 4 days until distinct colonies were formed. Eight white colonies for each transformation were picked and plasmid integration in the yeast genome was confirmed by PCR.

Isolated clones were individually inoculated into 10 mL of BMGY medium (Buffered Glycerol-complex Medium, 1% yeast extract; 2% peptone; 100 mM potassium phosphate, pH 6.0; 1.34% YNB-Yeast Nitrogen Base; 0.0004% biotin; 1% glycerol) in 50 mL conical tubes. The cells were grown for 48 hr at 28° C. with vigorous shaking at 250 rpm. Then, the cultures were centrifuged at 1,500 g for 5 min at room temperature, the cell pellets were resuspended in 2 mL of BMMY medium (Buffered Methanol-complex Medium, 1% yeast extract; 2% peptone; 100 mM potassium phosphate, pH 6.0; 1.34% YNB; 0.0004% biotin; 0.5% methanol) and cultured at 28° C. with shaking at 250 rpm to induce the expression. After continuous cultivation for 72 hr with daily addition of 0.5% methanol, cells were harvested by centrifuging for 10 min at 1500 g. Supernatant was transferred to a separate tube and both the supernatant and cell pellet were stored at −80° C. until ready for assay. Supernatants and cell pellets were analyzed for protein expression by SDS-PAGE Coomassie blue staining and Western blot. Our data showed that PichiaPink strain 2(ade2, pep4) supported the highest level of expression for FADS15, 12 and 9-I.

Example 4

Expression Condition Optimization and Protein Analysis

Individual colonies of *P. pastoris*-FADS15, FADS12 and FADS9-I were inoculated into 10 mL of BMGY medium in 50 mL conical tubes and cultured for 48 hr at 28° C. at shaking speed of 250 rpm. Then, 2.5 mL of culture were inoculated into 50 mL of BMGY medium in 250-mL volume shaker flasks and grown at 28° C. for 24 hr at 250 rpm. The cells were collected by centrifugation at 1500 g for 10 min, and resuspended in 10 mL induction medium (BMMY medium with 0.5% methanol) in a 100-mL shaker flask. The induction of protein expression was performed for 96 hr at 28° C. with 250 rpm agitation and daily addition of 0.5% methanol. Samples were collected at 0, 6, 24, 48, 72 and 96 hr for measuring cell density at $OD_{600}$, wet cell weight and total protein concentration, and for Western blot analysis of desaturase expression levels.

The cell pellets and supernatants were collected by centrifuging 100 μL cell culture at 1500 g for 10 min. Cell pellets were resuspended in 100 μL lysis buffer (20 mM Tris. Cl pH7.9, 1 mM EDTA, 5% Glycerol) with an equal volume of 0.5 mm Glass Beads (Biospec products, Inc.), and vortexed for 10 min at 4° C. Cell lysates were mixed with 4×SDS sample buffer and heated for 5 min at 95° C. About 5 μl sample was loaded onto Mini-Protein Precast Gels (4-15%, Bio-Rad Laboratories, Cat #456-1086), and ran for 40 min at 150 V. Then, the SDS-PAGE gels were used for Coomassie blue stain, Invision His-Tag in-gel stain (Invitrogen) or Western blot.

For Western blot analysis, protein gels were transferred onto a nitrocellulose transfer membrane (Schleicher & Schuell GmbH, Germany) by electroblotting (100 V, 2 hr) using Mini Trans-Blot electrophoretic transfer cell (Bio-Rad Laboratories). The membrane was blocked with 3% BSA in TBST (150 mM NaCl, 10 mM Tris-Cl pH 7.5, 0.05% Tween20), and probed with mouse Penta•His antibody (Invitrogen) followed by HRP-conjugated goat anti-mouse IgG (GE Healthcare). Blots were then incubated with enhanced chemiluminescence reagent (ECL, GE healthcare) and analyzed using Fluorchem E (Cell Biosciences, Inc.).

The total protein concentration was determined with Pierce BCA protein assay kit (Thermo Scientific). The quantification of target protein on Coomassie blue stained gel was performed using known concentrations of BSA as standard, and analyzed with the AlphaView SA software (Cell Biosciences, Inc.).

To determine potential toxicity of recombinant proteins, we first examined cell growth density, weight and total protein synthesis of the PichiaPink pPinkα-HC-FADS clones. The recombinant PichiaPink pPinkα-HC-FADS cells had growth characteristics similar to the control (FIG. 5A). A time course experiment showed that desaturase expression was detectable after 24 hr induction with 0.5% methanol and remained high for at least 72 hr post-induction (FIG. 5B). There were no significant differences in protein expression when cells were induced at different temperatures (16° C., 22° C., 28° C.) or with a different concentration of methanol (0.5%, 1%). Therefore, we used an optimized procedure as described in the Materials and Methods for the expression of recombinant desaturase. Under this condition, expression levels of recombinant desaturase proteins reached approximately 130 mg/L of culture for FADS15, 110 mg/L for FADS12 and 350 mg/L for FADS9-I (FIG. 5C).

Example 5

Protein Purification

All purification procedures were performed at 4° C. Cells harvested from 800 μL of culture were suspended in 800 μL of lysis buffer. After addition of 0.5 mm glass beads to the cell suspension, P. pastoris cells were disrupted by vortexing at 4° C. for 10 min Cell lysis efficiency was usually more than 95% evaluated using a light microscope. Intact cells and cell debris were removed from the membrane suspension by low speed centrifugation (500 g, 10 min at 4° C.). Then various centrifugation speeds and time (1,000 g for 10 min; 10,000 g for 10 min; 10,000 g for 20 min; 20,000 g for 10 min; 20,000 g for 20 min) were used to determine the best centrifugation conditions for collecting the membrane fraction.

Fractions containing recombinant desaturases were solubilized in buffer, containing 20 mM Tris.Cl, pH 7.9, 500 mM NaCl, 10% glycerol, 0.1 mM EDTA, and different concentrations (0.5%, 1%, 2%) of various detergents (Tween 20, Tween 80, Nonidet P-40, DDM, Fos-Choline 12, Fos-Choline 16) at 4° C. for different times (0.5, 1, 1.5, 2 hr and overnight). The insoluble materials were removed by centrifugation at 25,000 g for 30 min at 4° C.

Optimized culture and protein solubilization conditions were used for the subsequent purification process. His Mag Sepharose™ Ni affinity beads (GE Healthcare) were washed with binding buffer (20 mM Tris.Cl, pH 7.9, 500 mM NaCl, 10% glycerol, 0.1 mM EDTA, 0.5% Fos-Choline 16, 5 or 20 mM imidazole) and added to the solubilized fractions after detergent incubation. The bead-protein sample mixtures were incubated for 45 min at 4° C. with end-over-end mixing. After washing three times with binding buffer containing 5 mM or 20 mM imidazole, desaturase enzymes were eluted with elution buffer (20 mM Tris.Cl, pH 7.9, 500 mM NaCl, 10% glycerol, 0.1 mM EDTA, 0.5% Fos-Choline 16, 500 mM imidazole). The purified FADS15, FADS12 and FADS9-I proteins were stored at −80° C. in aliquots. The quantity and quality of these purified enzymes were analyzed by SDS-PAGE and desaturase activity assay.

In order to solubilize and purify the recombinant desaturases from cell membrane for in vitro enzymatic activity, we first tested conditions to enrich the cell membrane containing recombinant FADS15, FADS12 and FADS9-I. Different centrifugation speeds and times were examined for the separation of the membrane fractions containing target proteins. Efficient recovery of each recombinant desaturase produced in P. pastoris was achieved by centrifuging the cell homogenates at 500 g for 10 min to remove cell debris, then at 10,000 g for 10 min to collect membrane fractions (FIG. 6).

Solubilization of membrane proteins requires the presence of detergents. Therefore, we tested the conditions for solubilization of the recombinant FADS15, FADS12 and FADS9-I from enriched cell membrane fractions using a panel of detergents: Tween-20, Tween-80, NP-40, n-Dodecyl-β-D-maltoside (DDM), Fos-Choline 12 or Fos-Choline 16. After treatment with 1% (w/v) of Fos-Choline 12 or Fos-Choline 16, FADS9-I and FADS12 were totally solubilized, and approximately 50% and 80% of FADS15 was solubilized with Fos-Choline 12 and Fos-Choline 16, respectively (FIG. 7A). Tween-20, Tween-80, NP-40 and DDM had little effect on extracting these desaturase enzymes from the membrane. In addition, we noticed that FADS9-I protein degradation occurred during protein solubilization. This phenomenon was visible for proteins solubilized by both Fos-Choline 12 and 16. Thus, we investigated detergent incubation time during solubilization to optimize for the least protein degradation. Our results showed that the solubilization of FADS9-I protein reached its maximum level after incubation with detergent for 1.5 hr. Degradation of desaturase protein increased after more than 3 hr of incubation (FIG. 7B). To maximize the ratio of intact vs. degraded proteins, we used 1.5 hr as our standard detergent incubation time for protein solubilization. We also compared the effect of detergent concentrations on protein solubilization efficiency and found that 0.5%, 1% or 2% of Fos-Choline 16 had similar effects. Taken together, our results indicate that all three recombinant desaturase enzymes can be solubilized efficiently from the cell membrane with 0.5% Fos-Choline 16 for 1.5 hr at 4° C.

Solubilized FADS15, FADS12 and FADS9-I were affinity-purified on His Mag Sepharose Ni beads (GE healthcare) with aims of high purity or high yield. High purity (>95%) was achieved after one step purification using the His Mag Sepharose Ni beads with high stringency wash before elution (FIG. 7C). High yield (2-fold higher than that in the high purity process) was achieved with low stringency wash. Yield and quantity of each desaturase enzyme are summarized in Table 2. Our estimated yields of desaturases with purity>95% are approximately 22.5 mg/L for FADS15, 12 mg/L for FADS12 and 188 mg/L for FADS9-I.

TABLE 2

Purification of *M. alpina* desaturases

| | | FADS15 protein | | | FADS12 protein | | | FADS9-I protein | | |
|---|---|---|---|---|---|---|---|---|---|---|
| Process | Vol (μL) | Con. (mg/L) | Total (μg) | Yield (%) | Con. (mg/L) | Total (μg) | Yield (%) | Con. (mg/L) | Total (μg) | Yield (%) |
| Cell lysates | 200 | 130.0 | 26.0 | 100.0 | 110.0 | 22.0 | 100.0 | 350.0 | 70.0 | 100.0 |
| Centrifugal collections (500-10 kg) | 200 | 112.0 | 22.4 | 86.2 | 82.0 | 16.0 | 72.7 | 254.0 | 50.8 | 72.6 |
| Detergent treatment extracts | 200 | 76.0 | 15.2 | 58.5 | 74.8 | 15.0 | 68.2 | 223.0 | 44.6 | 63.7 |
| Ni-NTA (20 mM ID) | 40 | 22.5 | 0.9 | 3.5 | 12.0 | 0.5 | 2.3 | 188.0 | 7.5 | 10.7 |
| Ni-NTA (5 mM ID) | 100 | 10.5 | 1.1 | 4.2 | 7.5 | 0.8 | 3.6 | 185.0 | 18.5 | 26.4 |

ID: imidazole

Example 6

Desaturase Activity Assay

Approximately 20 mg of *P. pastoris* cell pellets were collected and used for each lipid extraction with the method of Bligh and Dyer (Bligh E G, Dyer W J (1959) A rapid method of total lipid extraction and purification. Can J Biochem Physiol 37: 911-917). under acidified conditions with pentadecanoic acid and heneicosanoic acid added as internal standards. The solvent from the extract was removed under a stream of nitrogen. Lipids were saponified in 1 mL of freshly prepared 5% ethanolic potassium hydroxide at 60° C. for 1 hr under an argon atmosphere. After cooling, 1 mL of water was added to the samples and non-saponifiable lipids were extracted into 3 mL of hexane. The aqueous layer was acidified with 220 μL of 6 M hydrochloric acid and the fatty acids extracted into 3 mL of hexane. After removing the hexane in a stream of nitrogen, fatty acids were converted to methyl esters by first treating with 1 mL of 0.5 M methanolic sodium hydroxide at 100° C. for 5 min under argon followed by 1 mL of 14% methanolic boron trifluoride at 100° C. for 5 min under argon (Metcalfe L D, Schmitz A A, Pelka J R (1966) Rapid preparation of fatty acids esters from lipids for gas chromatographic analysis. Analytical Chemistry 38: 514-515.). After cooling, the sample was mixed with 2 mL of hexane followed by 4 mL of saturated aqueous sodium chloride. After separating the phases, aliquots of the hexane layers were diluted 24-fold with hexane and then analyzed by GC/MS. One μL was injected in the splitless mode onto a 30 m×250 μm DB-WAXETR column (Agilent Technologies, Santa Clara, Calif.) with 0.25 μm film thickness. The temperature program was as follows: 100° C. for 2 min, ramp to 200° C. at 16° C. per min, hold for one min, ramp to 220° C. at 4° C. per min, hold one min, ramp to 260° C. at 10° C. per min, and hold for 11 min. Helium was the carrier gas at a constant flow of 1.5 mL/min. The mass spectrometer was operated in positive-ion electron impact mode with interface temperature 260° C., source temperature 200° C., and filament emission 250 μA. Spectra were acquired from m/z 50 to 450 with a scan time of 0.433 s. Lower-boiling fatty acid methyl esters were quantified using the pentadecanoic acid internal standard, whereas higher-boiling methyl esters were quantified using the heneicosanoic acid internal standard.

In Vivo Desaturase Activity Analysis:

Individual colonies of *P. pastoris*-FADS15, FADS12 and FADS9-I were cultured as described in the Recombinant protein expression section. Protein expression was induced for 72 hr with 0.5% methanol. Cell pellets were collected by centrifugation and stored at −80° C. for fatty acid analysis.

In Vitro Desaturase Activity Analysis:

20 μL of the purified protein was added to 200 μL of yeast EGY49 cell homogenate, prepared by breaking cells with 0.5 mm glass beads in lysis buffer (20 mM Tris-HCl pH7.9, 1 mM EDTA, 5% Glycerol). The enzyme reactions were performed at 28° C. for 3 h with shaking (250 rpm), and the assay mixture (220 μL) were stored at −80° C. for fatty acid analysis.

To determine the functional activity of the recombinant *M. alpina* desaturase in vivo, PichiaPink cells were cultured and induced to express desaturases. Fatty acid methyl esters (FAME) analysis of cell pellets showed that expression of recombinant desaturases in PichiaPink cells altered their fatty acid contents compared to the control. Table 3 shows the percentage increase of $C16:1^{\Delta 9}$, $C18:1^{\Delta 9}$, $C18:2^{\Delta 9,12}$ and $C18:2^{\Delta 9,12,15}$ compared to the negative control. The $C16:1^{\Delta 9}$ and $C18:1^{\Delta 9}$ were increased 40% and 20%, respectively, in PichiaPink cells expressing FADS9-I, suggesting that FAD9-I can insert the first double bond into both C16:0 and C18:0 with a preference for C16:0 as substrate. The $C18:2^{\Delta 9,12}$ content was 27% higher in cells expressing FADS12, suggesting that FADS12 can desaturate $C18:1^{\Delta 9}$ at the c12-position to produce $C18:2^{\Delta 9,12}$. There was a 5% increase in $C18:3^{\Delta 9,12,15}$ in cells expressing FADS15, suggesting that FADS15 can desaturate $C18:2^{\Delta 9,12}$ at the c15-position to produce $C18:3^{\Delta 9,12,15}$. These results suggest that the recombinant desaturases, FADS9-I, FADS12 and FADS15, were active in *P. pastoris*.

We used yeast EGY49 cell homogenate for our in vitro assay of recombinant desaturase activity. Our results showed that purified recombinant FADS12 converted $C18:1^{\Delta 9}$ to $C18:2^{\Delta 9,12}$ in vitro, and $C18:2^{\Delta 9,12}$ level was increased 116% compared to the control (Table 3). Activities of purified FADS9-I and FADS15 were relatively low in vitro.

TABLE 3

M. alpina desaturases in-vivo and in-vitro activities

| | In vivo | | | In vitro | | | |
|---|---|---|---|---|---|---|---|
| FADS9-I | | FADS12 | FADS15 | FADS9-I | | FADS12 | FADS15 |
| $C16:1^{\Delta9}$ (%[a]) | $C18:1^{\Delta9}$ (%) | $C18:2^{\Delta9,12}$ (%) | $C18:3^{\Delta9,12,15}$ (%) | $C16:1^{\Delta9}$ (%) | $C18:1^{\Delta9}$ (%) | $C18:2^{\Delta9,12}$ (%) | $C18:3^{\Delta9,12,15}$ (%) |
| 40 ± 6 | 20 ± 7 60 ± 7[b] | 27 ± 4 | 5 ± 3 | 6 ± 8 | 7 ± 7 13 ± 8 | 116 ± 40 | 8 ± 4 |

[a]Percent increase over control;
[b]Sum of two products

SEQUENCE LISTING

<160> NUMBER OF SEQ ID NOS: 14

<210> SEQ ID NO 1
<211> LENGTH: 1212
<212> TYPE: DNA
<213> ORGANISM: Mortierella alpina

<400> SEQUENCE: 1

```
atggccccc ctcacgttgt cgacgagcaa gtacgacgca gaatcgtcgt cgaggacgag      60
atccagtcca agaagcagtt tgagcgcaac tatgtgccta tggactttac aatcaaggag     120
attcgagatg cgatcccagc ccacctcttc atccgtgata ccacaaagtc gatcctgcat     180
gtcgtcaagg atctggtcac tatcgccatc gttttttact gtgcaacctt catcgagact     240
ctgccctcgc tcgctctgag agttcctgcc tggatcacct actggatcat ccaaggaact     300
gtcatggtcg gccctggat tctggcccac gagtgcggcc atggagcgtt ctcggacagc     360
aagacgatca acaccatctt tggatgggtc cttcactctg ctcttttggt gccctaccag     420
gcttgggcca tgtcgcattc aagcaccac aagggcactg gatccatgag caaggatgtc     480
gttttcatcc ctgccactcg atcctacaag ggccttcccc cactggagaa gcctgccgcg     540
gaagaggagg tttggagca ggagcatcac caccatgaag agtccatctt tgctgagact     600
cccatctaca ctctcggagc gctttttttc gtcctgacct gggatggcc cttgtacttg     660
atcatgaact ttctggaca cgaagcccct cactgggtca accattcca gacggtcgcc     720
cctctgtatg agcctcacca gcgcaagaac attttctact ccaactgcgg cattgtcgct     780
atgggctcga tcctcactta cctctcgatg gtcttctcgc ccttgactgt gttcatgtac     840
tatggcatcc cctacctcgg agtcaatgct tggatcgtct gcatcaccta tctccagcac     900
accgatccca aggtgcctca tttccgtgat aacgagtgga acttccagcg cggtgctgcc     960
tgcactatcg accgatcctt cggtaccatt gtcaaccact gcaccacca cattggtgac    1020
tctcatcaat gtcatcatat gttctcgcag atgcccttct acaacgccgt tgaggctaca    1080
aagcatctca aagccaagct tggcaagtac tacatatttg acgacactcc cattgccaag    1140
gccctctacc gcaattggag agagtgcaaa ttcgtggagg acgagggaga cgtagtgttc    1200
tacaagcatt aa                                                        1212
```

<210> SEQ ID NO 2
<211> LENGTH: 403
<212> TYPE: PRT
<213> ORGANISM: Mortierella alpina

<400> SEQUENCE: 2

```
Met Ala Pro Pro His Val Val Asp Glu Gln Val Arg Arg Ile Val
 1               5                  10                  15

Val Glu Asp Glu Ile Gln Ser Lys Lys Gln Phe Glu Arg Asn Tyr Val
             20                  25                  30

Pro Met Asp Phe Thr Ile Lys Glu Ile Arg Asp Ala Ile Pro Ala His
         35                  40                  45

Leu Phe Ile Arg Asp Thr Thr Lys Ser Ile Leu His Val Val Lys Asp
 50                  55                  60

Leu Val Thr Ile Ala Ile Val Phe Tyr Cys Ala Thr Phe Ile Glu Thr
 65                  70                  75                  80

Leu Pro Ser Leu Ala Leu Arg Val Pro Ala Trp Ile Thr Tyr Trp Ile
                 85                  90                  95

Ile Gln Gly Thr Val Met Val Gly Pro Trp Ile Leu Ala His Glu Cys
                100                 105                 110

Gly His Gly Ala Phe Ser Asp Ser Lys Thr Ile Asn Thr Ile Phe Gly
                115                 120                 125

Trp Val Leu His Ser Ala Leu Leu Val Pro Tyr Gln Ala Trp Ala Met
        130                 135                 140

Ser His Ser Lys His His Lys Gly Thr Gly Ser Met Ser Lys Asp Val
145                 150                 155                 160

Val Phe Ile Pro Ala Thr Arg Ser Tyr Lys Gly Leu Pro Pro Leu Glu
                165                 170                 175

Lys Pro Ala Ala Glu Glu Val Leu Glu Gln His His His His His His
                180                 185                 190

Glu Glu Ser Ile Phe Ala Glu Thr Pro Ile Tyr Thr Leu Gly Ala Leu
        195                 200                 205

Phe Phe Val Leu Thr Leu Gly Trp Pro Leu Tyr Leu Ile Met Asn Phe
        210                 215                 220

Ser Gly His Glu Ala Pro His Trp Val Asn His Phe Gln Thr Val Ala
225                 230                 235                 240

Pro Leu Tyr Glu Pro His Gln Arg Lys Asn Ile Phe Tyr Ser Asn Cys
                245                 250                 255

Gly Ile Val Ala Met Gly Ser Ile Leu Thr Tyr Leu Ser Met Val Phe
                260                 265                 270

Ser Pro Leu Thr Val Phe Met Tyr Tyr Gly Ile Pro Tyr Leu Gly Val
        275                 280                 285

Asn Ala Trp Ile Val Cys Ile Thr Tyr Leu Gln His Thr Asp Pro Lys
        290                 295                 300

Val Pro His Phe Arg Asp Asn Glu Trp Asn Phe Gln Arg Gly Ala Ala
305                 310                 315                 320

Cys Thr Ile Asp Arg Ser Phe Gly Thr Ile Val Asn His Leu His His
                325                 330                 335

His Ile Gly Asp Ser His Gln Cys His His Met Phe Ser Gln Met Pro
                340                 345                 350

Phe Tyr Asn Ala Val Glu Ala Thr Lys His Leu Lys Ala Lys Leu Gly
        355                 360                 365

Lys Tyr Tyr Ile Phe Asp Asp Thr Pro Ile Ala Lys Ala Leu Tyr Arg
        370                 375                 380

Asn Trp Arg Glu Cys Lys Phe Val Glu Asp Gly Asp Val Val Phe
385                 390                 395                 400

Tyr Lys His

<210> SEQ ID NO 3
```

<211> LENGTH: 1338
<212> TYPE: DNA
<213> ORGANISM: Mortierella alpina

<400> SEQUENCE: 3

```
atggcaactc ctcttccccc ctcctttgtc gtccctgcga cacagacgga aacccgcaga    60
gatcctctcc agcacgagga actgccccct ctcttcccg agaaaatcac catcttcaac    120
atctggagat atcttgacta caagcatgtt ctcggtctgg gctgacgcc tttgatcgct    180
ctctatggtc tcttgacgac cgagatccag acgaagacac tgatctggtc catcatctac    240
tattatgcta cgggacttgg catcacagca ggttaccatc gactctgggc catcgtgct     300
tacaacgcag gaccagccat gagcttcgtg ctcgcactgc tcggcgccgg tgcagttgaa    360
ggatctatca gtggtggtc ccgcggccac cgtgctcacc accgctggac tgacaccgag    420
aaggacccct acagcgctca ccgaggactc ttcttctcgc acattggctg gatgttgatc    480
aagcgccctg gatggaagat tggccatgcc gatgttgacg acctcaacaa gagcaaactc    540
gttcagtggc agcacaagaa ctaccttcct cttgttctta tcatgggtgt cgtcttcccc    600
acggttgttg ctggactcgg ctggggcgat tggcgtggag gctacttcta tgctgctatc    660
ctccgtcttg tctttgttca ccacgccacc ttctgtgtca actccctggc ccattggctc    720
ggtgatggac cctttgatga ccgccactct cccccgcgacc acttcatcac tgcctttgtc    780
actttgggag agggctacca caactttcat caccaattcc cccaggacta ccgcaacgct    840
atccgtttt accagtacga tcctaccaag tgggtcatcg ccctctgtgc tttctttggc    900
ctcgctacgc acctcaagac cttccctgag aatgaagtcc gcaagggtca gctccagatg    960
attgagaagc gtgtcctgga agaagacc aagctccagt ggggcactcc cattgccgat    1020
ctgcccattc tgagctttga ggacttccag catgcttgca aaaacgacaa caagaagtgg    1080
atcctcttgg agggtgtcgt ttacgacgtt gccgacttta tgaccgagca ccctggtggt    1140
gagaagtacc tcaagatggg cgtcggcaag gacatgaccg cagctttcaa cggcggtatg    1200
tacgatcaca gcaatgccgc cgcaacctg ctgagcttga tgcgcgtcgc cgtcgttgag    1260
tatggtggtg aggtggaggc acagaagaag aacccttcga tgcccatcta cggcactgac    1320
cacgtcaagg ccgaataa                                                 1338
```

<210> SEQ ID NO 4
<211> LENGTH: 445
<212> TYPE: PRT
<213> ORGANISM: Mortierella alpina

<400> SEQUENCE: 4

```
Met Ala Thr Pro Leu Pro Pro Ser Phe Val Val Pro Ala Thr Gln Thr
 1               5                  10                  15

Glu Thr Arg Arg Asp Pro Leu Gln His Glu Glu Leu Pro Pro Leu Phe
            20                  25                  30

Pro Glu Lys Ile Thr Val Tyr Asn Ile Trp Arg Tyr Leu Asp Tyr Lys
        35                  40                  45

His Val Phe Gly Leu Gly Leu Thr Pro Leu Ile Ala Leu Tyr Gly Leu
    50                  55                  60

Leu Thr Thr Glu Ile Gln Thr Lys Thr Leu Ile Trp Ser Ile Ile Tyr
65                  70                  75                  80

Tyr Tyr Ala Thr Gly Leu Gly Ile Thr Ala Gly Tyr His Arg Leu Trp
                85                  90                  95

Ala His Arg Ala Tyr Asn Ala Gly Pro Ala Met Ser Phe Val Leu Ala
```

```
                    100                 105                 110
Leu Leu Gly Ala Gly Ala Val Glu Gly Ser Ile Lys Trp Trp Ser Arg
        115                 120                 125
Gly His Arg Ala His His Arg Trp Thr Asp Thr Glu Lys Asp Pro Tyr
        130                 135                 140
Ser Ala His Arg Gly Leu Phe Phe Ser His Ile Gly Trp Met Leu Ile
145                 150                 155                 160
Lys Arg Pro Gly Trp Lys Ile Gly His Ala Asp Val Asp Asp Leu Asn
                165                 170                 175
Lys Ser Lys Leu Val Gln Trp Gln His Lys Asn Tyr Leu Pro Leu Val
                180                 185                 190
Leu Ile Met Gly Val Val Phe Pro Thr Val Val Ala Gly Leu Gly Trp
            195                 200                 205
Gly Asp Trp Arg Gly Gly Tyr Phe Phe Ala Ala Ile Leu Arg Leu Val
            210                 215                 220
Phe Val His His Ala Thr Phe Cys Val Asn Ser Leu Ala His Trp Leu
225                 230                 235                 240
Gly Asp Gly Pro Phe Asp Asp Arg His Ser Pro Arg Asp His Phe Ile
                245                 250                 255
Thr Ala Phe Val Thr Leu Gly Glu Gly Tyr His Asn Phe His His His Gln
                260                 265                 270
Phe Pro Gln Asp Tyr Arg Asn Ala Ile Arg Phe Tyr Gln Tyr Asp Pro
                275                 280                 285
Thr Lys Trp Val Ile Ala Leu Cys Ala Phe Phe Gly Leu Ala Thr His
            290                 295                 300
Leu Lys Thr Phe Pro Glu Asn Glu Val Arg Lys Gly Gln Leu Gln Met
305                 310                 315                 320
Ile Glu Lys Arg Val Leu Glu Lys Lys Thr Lys Leu Gln Trp Gly Thr
                325                 330                 335
Pro Ile Ala Asp Leu Pro Ile Leu Ser Phe Glu Asp Phe Gln His Ala
                340                 345                 350
Cys Lys Asn Asp Asn Lys Lys Trp Ile Leu Leu Glu Gly Val Val Tyr
                355                 360                 365
Asp Val Ala Asp Phe Met Thr Glu His Pro Gly Gly Glu Lys Tyr Ile
            370                 375                 380
Lys Met Gly Val Gly Lys Asp Met Thr Ala Ala Phe Asn Gly Gly Met
385                 390                 395                 400
Tyr Asp His Ser Asn Ala Ala Arg Asn Leu Leu Ser Leu Met Arg Val
                405                 410                 415
Ala Val Val Glu Phe Gly Gly Glu Val Glu Ala Gln Lys Lys Asn Pro
            420                 425                 430
Ser Met Pro Ile Tyr Gly Thr Asp His Val Lys Ala Glu
            435                 440                 445

<210> SEQ ID NO 5
<211> LENGTH: 39
<212> TYPE: DNA
<213> ORGANISM: Artificial Sequence
<220> FEATURE:
<223> OTHER INFORMATION: Primer sequences for PCR

<400> SEQUENCE: 5
atatcatatg atggcccccc ctcacgttgt cgacgagca                           39

<210> SEQ ID NO 6
```

```
<210> SEQ ID NO 7
<211> LENGTH: 39
<212> TYPE: DNA
<213> ORGANISM: Artificial Sequence
<220> FEATURE:
<223> OTHER INFORMATION: Primer sequences for PCR

<400> SEQUENCE: 6
atatattaat atggcacctc ccaacactat tgatgccgg                              39

<210> SEQ ID NO 7
<211> LENGTH: 39
<212> TYPE: DNA
<213> ORGANISM: Artificial Sequence
<220> FEATURE:
<223> OTHER INFORMATION: Primer sequences for PCR

<400> SEQUENCE: 7
atatcatatg atggcaactc ctcttccccc ctcctttgt                              39

<210> SEQ ID NO 8
<211> LENGTH: 33
<212> TYPE: DNA
<213> ORGANISM: Artificial Sequence
<220> FEATURE:
<223> OTHER INFORMATION: Primer sequences for PCR

<400> SEQUENCE: 8
atatggatcc taatgcttgt agaacactac gtc                                   33

<210> SEQ ID NO 9
<211> LENGTH: 34
<212> TYPE: DNA
<213> ORGANISM: Artificial Sequence
<220> FEATURE:
<223> OTHER INFORMATION: Primer sequences for PCR

<400> SEQUENCE: 9
atatggatcc ttacttcttg aaaaagacca cgtc                                  34

<210> SEQ ID NO 10
<211> LENGTH: 34
<212> TYPE: DNA
<213> ORGANISM: Artificial Sequence
<220> FEATURE:
<223> OTHER INFORMATION: Primer sequences for PCR

<400> SEQUENCE: 10
atatagatct ttattcggcc ttgacgtggt cagt                                  34

<210> SEQ ID NO 11
<211> LENGTH: 33
<212> TYPE: DNA
<213> ORGANISM: Artificial Sequence
<220> FEATURE:
<223> OTHER INFORMATION: Primer sequences for PCR

<400> SEQUENCE: 11
atatattgcg cacatcatca tcatcatcat cat                                   33

<210> SEQ ID NO 12
<211> LENGTH: 43
<212> TYPE: DNA
<213> ORGANISM: Artificial Sequence
<220> FEATURE:
<223> OTHER INFORMATION: Primer sequences for PCR

<400> SEQUENCE: 12
```

```
<210> SEQ ID NO 13
<211> LENGTH: 36
<212> TYPE: DNA
<213> ORGANISM: Artificial Sequence
<220> FEATURE:
<223> OTHER INFORMATION: Primer sequences for PCR

<400> SEQUENCE: 13
atatatggta ccttacttct tgaaaaagac cacgtc                        36

<210> SEQ ID NO 14
<211> LENGTH: 36
<212> TYPE: DNA
<213> ORGANISM: Artificial Sequence
<220> FEATURE:
<223> OTHER INFORMATION: Primer sequences for PCR

<400> SEQUENCE: 14
atatatggta ccttattcgg ccttgacgtg gtcagt                        36
```
atatgaattc atatttaaat taatgcttgt agaacactac gtc                43

(Note: the first sequence above with length 43 appears before SEQ ID NO 13.)

What is claimed is:

1. A process for producing a purified omega-3 desaturase, comprising:
   (a) constructing a pPinkα-HC vector containing cDNA molecule having the nucleotide sequence shown as SEQ ID NO:1;
   (b) transforming a suitable host cell with said vector of Step (a), wherein said host cell is a yeast cell;
   (c) culturing said host cell under conditions which allow the expression of said omega-3 desaturase by said host cell; and
   (d) isolating said omega-3 desaturase from the culture media of Step (c);
   wherein said purified omega-3 desaturase is produced.

2. The process of claim 1, said yeast cell is *Pichia pastoris*.

3. The process of claim 2, said *Pichia pastoris* is selected from a group of hosts consisting of PichiaPink strain 1, PichiaPink strain 2, PichiaPink strain 3, and PichiaPink strain 4.

4. The process of claim 3, said omega-3 desaturase has the amino acid sequence shown as SEQ ID NO:2.

* * * * *